(12) United States Patent
Lee et al.

(10) Patent No.: US 10,842,205 B2
(45) Date of Patent: Nov. 24, 2020

(54) APPAREL THERMO-REGULATORY SYSTEM

(71) Applicant: NIKE, Inc., Beaverton, OR (US)

(72) Inventors: Hoonjoo Lee, Washington, DC (US); Matthew D. Nordstrom, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 149 days.

(21) Appl. No.: 15/786,879

(22) Filed: Oct. 18, 2017

(65) Prior Publication Data

US 2018/0110266 A1    Apr. 26, 2018

Related U.S. Application Data

(60) Provisional application No. 62/410,453, filed on Oct. 20, 2016.

(51) Int. Cl.
*A45F 5/02* (2006.01)
*A41D 13/005* (2006.01)
(Continued)

(52) U.S. Cl.
CPC ........... *A41D 13/005* (2013.01); *A41D 1/005* (2013.01); *A41D 13/0025* (2013.01); *A41D 27/28* (2013.01); *A45F 5/02* (2013.01); *A61B 5/6804* (2013.01); *F25B 21/04* (2013.01); *G08B 21/0453* (2013.01); *A41D 1/002* (2013.01); *F25B 21/02* (2013.01); *H01L 35/30* (2013.01)

(58) Field of Classification Search
CPC ................. A61B 5/6804; A61B 5/0402; A61F 2007/0075; A41D 13/005; A41D 13/0051; A41D 13/0053

USPC ............................................. 62/3.5; 600/301
See application file for complete search history.

(56) References Cited

U.S. PATENT DOCUMENTS

| | | |
|---|---|---|
| 1,452,052 A | 4/1923 | Nalle |
| 1,553,461 A | 9/1925 | Negromanti |

(Continued)

FOREIGN PATENT DOCUMENTS

| | | | |
|---|---|---|---|
| CA | 2944485 A1 * | 10/2015 | ............ D06M 15/00 |
| CN | 1976632 A | 6/2007 | |

(Continued)

OTHER PUBLICATIONS

English language translation of DE202015103917, to King's Metal Fiber Technologies, Aug. 14, 2015, translation accessed via espacenet.com (last visited Feb. 10, 2020).*

(Continued)

*Primary Examiner* — Alissa L Hoey
*Assistant Examiner* — Patrick J. Lynch
(74) *Attorney, Agent, or Firm* — Shook, Hardy & Bacon LLP

(57) ABSTRACT

Aspects herein are directed to an apparel thermo-regulatory system that actively heats or cools a wearer. The apparel thermo-regulatory system comprises an apparel item, a dimensionally stable frame comprising at least one aperture that is affixed to an outer-facing surface of the apparel item at a predetermined location, an absorbent material applied to an exposed face of the dimensionally stable frame, and at least one thermoelectric module that is releasably positioned within the aperture of the dimensionally stable frame.

9 Claims, 16 Drawing Sheets

(51) Int. Cl.
  *A41D 27/28* (2006.01)
  *A41D 1/00* (2018.01)
  *A41D 13/002* (2006.01)
  *F25B 21/04* (2006.01)
  *A61B 5/00* (2006.01)
  *G08B 21/04* (2006.01)
  *F25B 21/02* (2006.01)
  *H01L 35/30* (2006.01)

(56) References Cited

U.S. PATENT DOCUMENTS

| | | | |
|---|---|---|---|
| 2,203,017 A | 6/1940 | Illsche | |
| 2,798,493 A | 7/1957 | Sukacev | |
| 2,798,494 A | 7/1957 | Sukacev | |
| 2,991,627 A | 7/1961 | Suits | |
| 3,085,405 A | 4/1963 | Frantti | |
| 3,449,802 A | 6/1969 | Mackey | |
| 3,602,001 A | 8/1971 | Bauer et al. | |
| 3,737,620 A | 6/1973 | Harvey | |
| 3,892,225 A | 7/1975 | Twose | |
| 4,369,528 A * | 1/1983 | Vest | A41D 13/1236 2/114 |
| 4,470,263 A | 9/1984 | Lehovec et al. | |
| 4,483,021 A | 11/1984 | McCall | |
| 4,551,857 A | 11/1985 | Galvin | |
| 4,777,802 A | 10/1988 | Feher | |
| 4,846,176 A | 7/1989 | Golden | |
| 4,930,317 A | 6/1990 | Klein | |
| 4,944,044 A | 7/1990 | Zarotti | |
| 5,033,170 A | 7/1991 | Ewert | |
| 5,092,129 A | 3/1992 | Bayes et al. | |
| 5,127,896 A | 7/1992 | De Gaston | |
| 5,197,294 A | 3/1993 | Galvan et al. | |
| 5,490,309 A | 2/1996 | Velasquez et al. | |
| 5,603,728 A | 2/1997 | Pachys | |
| 5,617,587 A | 4/1997 | Marchbanks | |
| 5,655,374 A | 8/1997 | Santilli et al. | |
| 5,772,620 A * | 6/1998 | Szlema | A61F 5/0118 128/878 |
| 5,800,490 A | 9/1998 | Patz et al. | |
| RE36,242 E | 6/1999 | Apisdorf | |
| 5,970,718 A | 10/1999 | Arnold | |
| 6,023,932 A | 2/2000 | Johnston | |
| 6,080,690 A | 6/2000 | Lebby et al. | |
| 6,125,636 A | 10/2000 | Taylor et al. | |
| 6,183,855 B1 | 2/2001 | Buckley | |
| 6,230,501 B1 | 5/2001 | Bailey et al. | |
| 6,297,728 B1 | 10/2001 | Rippbauer | |
| 6,362,740 B1 | 3/2002 | Jung | |
| 6,382,208 B2 | 5/2002 | Reedy et al. | |
| 6,510,696 B2 | 1/2003 | Guttman et al. | |
| 6,523,354 B1 | 2/2003 | Tolbert | |
| 6,557,353 B1 | 5/2003 | Fusco et al. | |
| 6,730,115 B1 | 5/2004 | Heaton | |
| 6,739,138 B2 | 5/2004 | Saunders et al. | |
| 6,791,004 B2 | 9/2004 | Sprengard-Eichel et al. | |
| 6,823,678 B1 | 11/2004 | Li | |
| 6,840,955 B2 | 1/2005 | Ein | |
| 6,855,410 B2 | 2/2005 | Buckley | |
| 6,910,931 B1 | 6/2005 | Nakase | |
| 6,915,641 B2 | 7/2005 | Harvie | |
| 6,927,316 B1 | 8/2005 | Faries, Jr. et al. | |
| 6,941,775 B2 | 9/2005 | Sharma | |
| 6,942,015 B1 | 9/2005 | Jenkins | |
| 6,948,322 B1 | 9/2005 | Giblin | |
| 7,000,682 B2 | 2/2006 | Chambers | |
| 7,037,326 B2 | 5/2006 | Lee | |
| 7,124,593 B2 | 10/2006 | Feher | |
| 7,143,451 B2 | 12/2006 | Lundgren | |
| 7,186,957 B2 | 3/2007 | Martin | |
| 7,249,464 B1 | 7/2007 | Watson | |
| 7,272,946 B2 | 9/2007 | Ichigaya | |
| 7,296,304 B2 | 11/2007 | Goldsborough | |
| 7,331,183 B2 | 2/2008 | Askew | |
| 7,363,765 B2 | 4/2008 | Szczesuil et al. | |
| 7,571,615 B1 | 8/2009 | Bikes | |
| 7,592,276 B2 | 9/2009 | Hill et al. | |
| 7,727,267 B2 | 6/2010 | Lachenbruch | |
| 7,744,640 B1 | 6/2010 | Faries, Jr. et al. | |
| 7,816,632 B2 | 10/2010 | Bourke, III et al. | |
| 7,827,620 B2 | 11/2010 | Feher | |
| 7,874,666 B2 | 1/2011 | Xu et al. | |
| 8,001,794 B2 | 8/2011 | Windisch | |
| 8,087,254 B2 | 1/2012 | Arnold | |
| 8,104,094 B2 | 1/2012 | Uttrachi | |
| 8,128,675 B2 | 3/2012 | Nahhas | |
| 8,191,180 B2 | 6/2012 | Berry | |
| 8,267,983 B2 | 9/2012 | Rogers et al. | |
| 8,281,609 B1 | 10/2012 | Rothschild et al. | |
| 8,308,489 B2 | 11/2012 | Lee et al. | |
| 8,314,283 B2 | 11/2012 | Kingsford et al. | |
| 8,397,517 B2 | 3/2013 | Monk | |
| 8,397,518 B1 | 3/2013 | Vistakula | |
| 8,690,934 B2 | 4/2014 | Boyden et al. | |
| 8,709,058 B1 | 4/2014 | Harsy | |
| 8,715,329 B2 | 5/2014 | Robinson et al. | |
| 8,753,383 B2 | 6/2014 | Parish et al. | |
| 8,907,251 B2 | 12/2014 | Larsen et al. | |
| 8,933,426 B2 | 1/2015 | Rees | |
| 9,029,736 B2 | 5/2015 | Lavin, Jr. | |
| 9,065,016 B2 | 6/2015 | Peter et al. | |
| 9,089,400 B2 | 7/2015 | Nofzinger | |
| D738,995 S | 9/2015 | Shapiro et al. | |
| 9,122,082 B2 | 9/2015 | Abreu | |
| 9,142,839 B2 | 9/2015 | Revol Cavalier | |
| 9,175,887 B2 | 11/2015 | Lau | |
| 2002/0069906 A1 | 6/2002 | Macris | |
| 2002/0156509 A1 | 10/2002 | Cheung | |
| 2004/0055120 A1 | 3/2004 | Gillis | |
| 2004/0211189 A1 | 10/2004 | Arnold | |
| 2005/0000231 A1 | 1/2005 | Lee | |
| 2005/0131504 A1 | 6/2005 | Kim | |
| 2005/0149153 A1 | 7/2005 | Nakase | |
| 2006/0048520 A1 | 3/2006 | Huang et al. | |
| 2006/0052734 A1* | 3/2006 | Evans | A61F 5/0111 602/27 |
| 2006/0191270 A1 | 8/2006 | Warren | |
| 2006/0280948 A1* | 12/2006 | Moreshead | B32B 5/024 428/411.1 |
| 2007/0084496 A1* | 4/2007 | Edey | H01L 35/00 136/201 |
| 2007/0113564 A1 | 5/2007 | Whitney et al. | |
| 2007/0199137 A1 | 8/2007 | Numes Ramos De Carvalho et al. | |
| 2007/0285868 A1* | 12/2007 | Lindberg | A61B 5/0245 600/382 |
| 2007/0288074 A1 | 12/2007 | Cazzini | |
| 2008/0015665 A1 | 1/2008 | Lachenbruch | |
| 2008/0046047 A1 | 2/2008 | Jacobs | |
| 2008/0091090 A1* | 4/2008 | Guillory | A61B 5/0478 600/301 |
| 2008/0109941 A1 | 5/2008 | Moreshead | |
| 2008/0155991 A1 | 7/2008 | Lee | |
| 2008/0168775 A1 | 7/2008 | Windheim et al. | |
| 2008/0250547 A1 | 10/2008 | Frank | |
| 2009/0055987 A1 | 3/2009 | Becker et al. | |
| 2009/0071169 A1 | 3/2009 | Kao | |
| 2009/0151043 A1 | 6/2009 | Moreshead | |
| 2010/0005572 A1 | 1/2010 | Chaplin | |
| 2010/0084125 A1 | 4/2010 | Goldstein et al. | |
| 2010/0107657 A1 | 5/2010 | Vistakula | |
| 2010/0198322 A1 | 8/2010 | Joseph et al. | |
| 2010/0281883 A1 | 11/2010 | Romano | |
| 2011/0005236 A1 | 1/2011 | Chang et al. | |
| 2011/0078845 A1 | 4/2011 | McKinney | |
| 2011/0127248 A1 | 6/2011 | Moreshead | |
| 2011/0128726 A1 | 6/2011 | Moreshead | |
| 2011/0130813 A1 | 6/2011 | Moreshead | |
| 2011/0172750 A1 | 7/2011 | Cassidy et al. | |
| 2011/0192172 A1 | 8/2011 | Delacruz | |
| 2011/0259028 A1 | 10/2011 | Lee | |
| 2011/0276114 A1 | 11/2011 | Faridoon | |
| 2011/0277485 A1 | 11/2011 | Yang et al. | |

(56) References Cited

U.S. PATENT DOCUMENTS

| | | | |
|---|---|---|---|
| 2012/0018418 A1 | 1/2012 | Shantha et al. | |
| 2012/0031582 A1 | 2/2012 | Sullivan | |
| 2012/0071804 A1* | 3/2012 | Philip | A61F 5/0118 602/21 |
| 2012/0124719 A1 | 5/2012 | Michlitsch et al. | |
| 2012/0227432 A1 | 9/2012 | Creech et al. | |
| 2012/0227778 A1 | 9/2012 | Leonov | |
| 2012/0318781 A1* | 12/2012 | Lavin, Jr. | A41D 13/005 219/211 |
| 2013/0008181 A1 | 1/2013 | Makansi et al. | |
| 2013/0019503 A1 | 1/2013 | Vogt | |
| 2013/0032025 A1 | 2/2013 | Wright | |
| 2013/0087180 A1 | 4/2013 | Stark et al. | |
| 2013/0090683 A1 | 4/2013 | Schock | |
| 2013/0116759 A1 | 5/2013 | Levinson et al. | |
| 2013/0238042 A1 | 9/2013 | Gildersleeve et al. | |
| 2013/0268032 A1 | 10/2013 | Neev | |
| 2013/0274587 A1* | 10/2013 | Coza | A61B 5/6804 600/409 |
| 2013/0312806 A1 | 11/2013 | Carroll | |
| 2013/0333394 A1 | 12/2013 | Chow | |
| 2013/0338472 A1* | 12/2013 | Macia Barber | A61B 5/04085 600/388 |
| 2014/0013545 A1 | 1/2014 | Pernu et al. | |
| 2014/0060607 A1 | 3/2014 | Wu et al. | |
| 2014/0090150 A1 | 4/2014 | Skertic | |
| 2014/0101831 A1 | 4/2014 | Balzano | |
| 2014/0130225 A1 | 5/2014 | Balzano | |
| 2014/0137569 A1 | 5/2014 | Parish et al. | |
| 2014/0182050 A1 | 7/2014 | Ameil et al. | |
| 2014/0221889 A1* | 8/2014 | Burns | A61F 5/0102 602/5 |
| 2014/0222121 A1 | 8/2014 | Spence et al. | |
| 2014/0236271 A1 | 8/2014 | Fronda et al. | |
| 2014/0259267 A1 | 9/2014 | Nordstrom | |
| 2014/0260331 A1 | 9/2014 | Lofy et al. | |
| 2014/0262774 A1* | 9/2014 | Bhatia | G01N 27/07 204/403.01 |
| 2014/0277220 A1 | 9/2014 | Brennan et al. | |
| 2014/0283276 A1 | 9/2014 | Johnson | |
| 2014/0318154 A1 | 10/2014 | Kobayashi | |
| 2014/0358203 A1 | 12/2014 | Li | |
| 2014/0358205 A1 | 12/2014 | Robke et al. | |
| 2014/0364771 A1* | 12/2014 | Pitts | A61B 5/6885 600/595 |
| 2015/0025305 A1 | 1/2015 | Stringer et al. | |
| 2015/0059042 A1 | 3/2015 | Aquino | |
| 2015/0067950 A1 | 3/2015 | Jennings | |
| 2015/0075185 A1 | 3/2015 | Sims | |
| 2015/0101788 A1 | 4/2015 | Smith et al. | |
| 2015/0119849 A1 | 4/2015 | Aronhalt et al. | |
| 2015/0157495 A1 | 6/2015 | Robst et al. | |
| 2015/0173445 A1 | 6/2015 | Gordon et al. | |
| 2015/0230527 A1* | 8/2015 | Branson | A41D 23/00 2/181 |
| 2015/0237927 A1 | 8/2015 | Nelson et al. | |
| 2015/0305677 A1* | 10/2015 | Berg | A61B 5/6804 600/388 |
| 2015/0359485 A1* | 12/2015 | Berg | A61B 5/6804 600/388 |
| 2016/0367213 A1* | 12/2016 | Fujita | A61B 5/02028 |
| 2017/0027053 A1* | 1/2017 | Moczygemba | H05K 1/0203 |
| 2017/0056650 A1* | 3/2017 | Cohen | A61N 1/08 |
| 2017/0196514 A1* | 7/2017 | Moltani | A61B 5/6804 |
| 2017/0319132 A1* | 11/2017 | Longinotti-Buitoni | A61B 5/0002 |
| 2018/0008195 A1* | 1/2018 | Vaitaitis | A61B 5/6804 |
| 2018/0249767 A1* | 9/2018 | Begriche | H05K 1/0283 |

FOREIGN PATENT DOCUMENTS

| | | |
|---|---|---|
| CN | 104536481 A | 4/2015 |
| DE | 19745889 A1 | 4/1999 |
| DE | 69701735 T2 | 2/2001 |
| DE | 102004032569 A1 | 1/2005 |
| DE | 202015103917 U1 | 8/2015 |
| EP | 1737052 A1 | 12/2006 |
| EP | 1854437 A1 | 11/2007 |
| EP | 2835070 A1 | 2/2015 |
| EP | 2865287 A1 | 4/2015 |
| GB | 2363803 A | 12/2001 |
| GB | 2430549 A | 3/2007 |
| GB | 2475922 A | 6/2011 |
| JP | 2000234584 A | 8/2000 |
| JP | 2008031581 A | 2/2008 |
| JP | 2012013238 A | 1/2012 |
| WO | 0139692 A2 | 7/2001 |
| WO | 2004111741 A1 | 12/2004 |
| WO | 2006055125 A1 | 5/2006 |
| WO | 2006075134 A1 | 7/2006 |
| WO | 2007110760 A2 | 10/2007 |
| WO | 2007116286 A2 | 10/2007 |
| WO | 2008095851 A2 | 8/2008 |
| WO | 2010085163 A1 | 7/2010 |
| WO | 2014179622 A1 | 11/2014 |
| WO | 2015013615 A2 | 1/2015 |
| WO | 2015036165 A1 | 3/2015 |
| WO | 2015102986 A | 7/2015 |
| WO | 2015103243 A1 | 7/2015 |
| WO | 2015112516 A1 | 7/2015 |
| WO | 2015148411 A1 | 10/2015 |
| WO | 2015149537 A1 | 10/2015 |

OTHER PUBLICATIONS

Millner, Jack, "Dieters rejoice! Weight-loss Clothing 'hacks' your metabolism to trick your body into burning 1,000 extra calories a Day, makers claim," dailymail.co.uk, Aug. 4, 2015 http://www.dailymail.co.uk/sciencetech/article-3184831/Dieters-rejoice-Weight-loss-CLOTHING-hacks-metabolism-trick-body-burning-1-000-extra-calories-DAY-,alers-claim.html.

Hu, Eric, Akif Kaynak, and Yuncang Li, "Development of a cooling fabric from conducting polymer coated fibres: Proof of concept," Synthetic metals 150.2 (2005): 139-143. http://dro.deakin.edu.au/eserv/DU:30002998/kaynak-developmentofacooling-2005.pdf.

Broutin, Jennifer, "Week 13: Final Project," MIT, fab.cba.mit.edu, accessed: Dec. 2015. http://fab.cba.mit.edu/classes/863.11/people/jenny.broutin/projects.html.

"Flexible Thermoelectric Generator Could Power Wearable Devices Using Body Heat," Electronics Cooling, electronics-cooling.com, Apr. 11, 2014. http://www.electronics-cooling.com/2014/04/thermoelectic-body-heat/.

"Engineers win grant to make smart clothes for personalized cooling and heating," UC San Diego, jacobsschool.ucsd.edu, accessed: Dec. 2015. http://jacobsschool.ucsd.edu/news/news_releases/release.sfe?id=1753.

Labarre, Suzanne, "Nanotech Clothing Warms in Winter, Cools in Summer," Fast Company, fastcodesign.com, Dec. 10, 2010. http://www.fastcodesign.com/1662859/nanotech-clothing-warms-in-winter-cools-in-summer.

A.A.K. "Don't forget to recharge your jacket." The Economist, economist.com, May 18, 2011. http://www.economist.com/blogs/babbage/2011/05/climate-controlled_clothing.

Sahta, I., et al. "The control of human thermal comfort by the smart clothing." SHS Web of Conferences. vol. 10. EDP Sciences, 2014. http://www.shs-conferences.org/articles/shsconf/pdf/2014//07/shsconf_shw2012_00040.pdf.

Jung, Ye-Lee, Young-Jin Chae, and Eun Kim. "Development of Cooling Garment for Extremely Hot Environment Using a Peltier Device and its Comfort Properties." Journal of the Korean Society of Clothing and Textiles 36.1 (2012): 1-11. http://ocean.kisti.re.kr/downfile/volume/ksct/GORHB4/2012/v36n1/GORHB4_2012_v36n1_1.pdf.

Bansevicius, R., R. Rackiene, and J. A. Virbalis. "The Body Cooling System Integrated into the Clothes." 2007. https://www.researchgate.net/profile/Juozapas_Virbalis/publication/228427247_The_body_cooling_system_integrated_into_the_clothes/links/0c960524bb3d0dc039000000.pdf.

(56) References Cited

OTHER PUBLICATIONS

International Search Report and Written Opinion dated Mar. 1, 2018 in International Patent Application No. PCT/US2017/057659, 16 pages.
International Preliminary Report on Patentability dated May 2, 2019 in International Patent Application No. PCT/US2017/057659, 9 pages.

\* cited by examiner

APPAREL THERMO-REGULATORY SYSTEM

CROSS-REFERENCE TO RELATED APPLICATIONS

This application, having U.S. application Ser. No. 15/786,879, filed Oct. 18, 2017, and entitled "Apparel Thermo-Regulatory System: claims the benefit of priority of U.S. Prov. App. No. 62/410,453, entitled "Apparel Thermo-Regulatory System," and filed Oct. 20, 2016. The entirety of the aforementioned application is incorporated by reference herein.

TECHNICAL FIELD

The present disclosure relates to an apparel thermo-regulatory system for actively cooling or heating a wearer when worn.

BACKGROUND

Maintaining persons such that their core body temperature stays within a predetermined range is important for optimizing performance whether athletic or otherwise. However, this may be difficult with traditional apparel.

BRIEF DESCRIPTION OF THE DRAWINGS

Examples of the present invention are described in detail below with reference to the attached drawing figures, wherein.

DETAILED DESCRIPTION

Figure 1:
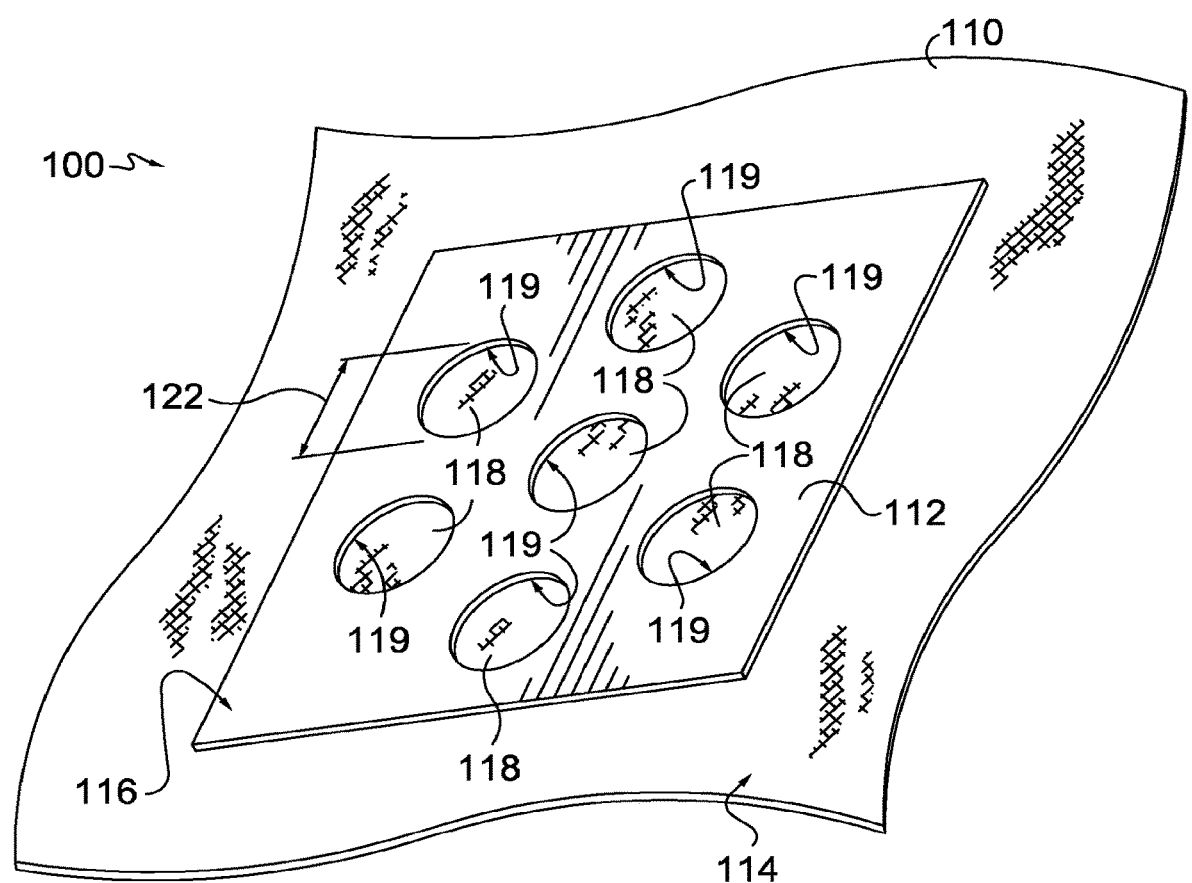
FIG. 1 illustrates a perspective view of an exemplary attachment structure for attaching a device to a flexible material in accordance with aspects herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

At a high level, aspects herein relate to an apparel thermo-regulatory system configured to promote recovery from athletic exercise and/or to actively heat or cool a wearer to help maintain the wearer in an optimal temperature range thus facilitating, for example, job performance and/or athletic performance. Apparel thermo-regulatory systems described herein may be suitable for a wide range of applications such as, for example, athletes, firefighters, first responders, military personnel, and the like. More specifically, aspects herein contemplate an apparel thermo-regulatory system that utilizes thermoelectric modules (otherwise known as thermoelectric coolers, Peltier chips or devices, thermoelectric units, thermoelectric chips, and the like) integrated into an apparel item using one or more attachment structures to heat or cool a wearer. Before describing further aspects of this disclosure, a brief overview of thermoelectric modules and how they operate will be provided.

A thermoelectric module (TEM) is a solid-state heat pump that utilizes electrical energy to transfer heat from a cold side to a hot side of the TEM against a temperature gradient, using the Peltier effect. When used for cooling, heat is absorbed at the cold side by electrons as they pass from a low energy level in a p-type semiconductor element to a higher energy level in an n-type semiconductor element. A voltage differential between a positive connector and a negative connector of the TEM provides the electrical potential to move the electrons from the low energy level to the high energy level. At the hot side of the TEM, energy in the form of heat is released as the electrons move from the higher energy level back to the low energy level. TEMs have the advantage of switching from cooling to heating by reversing the polarity of the electrical supply. Thus, what may have formerly been the cold side of the TEM may become the hot side, and what may have formerly been the hot side of the TEM may become the cold side after the polarity is reversed. Thus, a single TEM may be used to both heat and cool.

For the TEM to function efficiently (i.e. to not consume excessive power), it is important to remove the heat that is generated at the hot side of the TEM. This can be a challenge when the TEMs are used in apparel as traditional heat sinks such as fans are not practical. Aspects herein contemplate an apparel thermo-regulatory system that uses evaporative heat transfer to dissipate heat from the hot side of the TEM. More particularly, aspects herein contemplate harnessing the wearer's own sweat or perspiration to remove the heat from the hot side of the TEM. A number of different approaches may be used to transport sweat from a first part of an apparel item to a second part of the apparel item where one or more TEMs are located. Once transported to the area where the TEMs are located, evaporation of the sweat helps to dissipate heat from the hot side of the TEMs. Moreover, because the hot side of the TEM is at a higher temperature than the wearer's body, more heat is forced into the ambient environment than would occur by sweating alone which may further help to cool the wearer.

Additional aspects of the apparel thermo-regulatory system contemplated herein comprise an attachment structure useable for attaching one or more devices, such as one or more TEMs to an apparel item. Because apparel items are generally formed of a flexible material, it may be challenging to attach more rigid structures, such as TEMs, to the apparel item without comprising the integrity, the physical characteristics (e.g., flexibility, pliability, drapability, and the like), and/or the functional characteristics (e.g., permeability, breathability, moisture-management characteristics, and the like) of the apparel item. Aspects herein contemplate a flexible, dimensionally stable frame integrated into the apparel item and configured to receive one or more devices such as TEMs. The dimensionally stable frame is integrated into the apparel item in such a way that it does not need to be removed prior to, for instance, washing. In this way, a wearer may don the apparel item, quickly attach the one or more devices to the integrated dimensionally stable frame, and begin, for example, working or exercising.

In exemplary aspects, the dimensionally stable frame comprises a first surface, a second surface opposite the first surface, and at least one aperture sized to receive a device such as a TEM. As used throughout this disclosure, the term "dimensionally stable" may be defined as a material that exhibits the property of being able to maintain its original dimensions while being used for its intended purpose. The first surface of the dimensionally stable frame is affixed to the outer-facing surface of the apparel item. In an exemplary aspect, an absorbent material may be applied to the second surface of the frame. As will be explained more fully below, the absorbent material may be used to collect perspiration and/or water and continually release it around the hot side of the TEMs to help remove heat from the TEMs. Further, in an exemplary aspect, the dimensionally stable frame may be perforated to enable perspiration located on the outer-facing surface of the apparel item to move through the dimensionally stable frame to the absorbent material.

Continuing, in use, one or more TEMs may be positioned adjacent an inner-facing surface of the apparel item and releasably mated with the aperture of the dimensionally stable frame. To facilitate the attachment of the TEM to the frame, the TEM may comprise a base portion having a first generally planar surface and a flange portion having a second generally planar surface opposite the first surface. The flange portion extends outward from the base portion to form a lip between the base portion and the flange portion. The aperture in the dimensionally stable frame may have an aperture size that is intermediate between the width of the base portion and that of the flange portion of the TEM. When the flange portion is positioned within the aperture of the dimensionally stable frame and a degree of pressure is applied, the flange portion is forced through the aperture and the lip engages with the aperture edges to maintain the TEM within the frame. In this configuration, because the TEM is inserted from an inner-facing side of the apparel item, and the dimensionally stable frame is affixed to the outer-facing side of the apparel item, a portion of the fabric of the apparel item covers the second surface of the TEM after it is mated with the aperture of the dimensionally stable frame. This may promote removal of heat from the TEM as explained more fully below.

Aspects herein further contemplate a thermoelectric module array (a TEM array). In exemplary aspects, the TEM array may comprise two or more TEMs that are physically and electrically coupled using a flexible substrate to which an electronic circuit is applied. A power supply unit may also be physically and electrically coupled to the TEMs using the flexible substrate. In exemplary aspects, the flexible substrate may comprise an electrically insulating polyimide film such as Kapton®. In one exemplary aspect, the TEM array may comprise six TEMs that are arranged radially around a seventh TEM to form a spoke-and-hub pattern. The polyimide film connects each of the six TEMs to the seventh TEM and may further connect the TEMs to a power supply unit such as a battery. This is just one exemplary pattern, and additional patterns are contemplated herein such as TEMs arranged in a linear pattern, a staggered pattern, an auxetic pattern, and the like. The TEM array described herein may comprise additional components such as temperature sensors for detecting the surface temperature of a wearer's skin, microprocessors and controllers for cycling the TEMs from an off state to an on state, and the like.

Additionally, aspects herein are directed to an apparel thermo-regulatory system comprising an apparel item, the dimensionally stable frame described above, and the TEM array previously described. In exemplary aspects, the apparel item may be formed of a wicking material. An exemplary wicking material may comprise Dri-FIT® by Nike, Inc. These types of materials typically wick moisture from an inner-facing surface of the material to an outer-facing surface of the material where it can evaporate. Continuing, the dimensionally stable frame may be applied to the outer-facing surface of the apparel item at one or more predetermined locations. In one exemplary aspect, the predetermined locations may correspond to high heat and/or sweat-producing areas of the human body as indicated by, for example, heat and sweat maps.

Continuing, the TEM array or other type of device array may be positioned adjacent to an inner-facing surface of the apparel item at the one or more predetermined locations, and the array may be releasably mated to the dimensionally stable frame. When used for cooling, the first planar surface of the base portion of each TEM comprises the "cold" side of the TEM and the second planar surface of the flange portion comprises the "hot" side of the TEM. When the apparel item is in an as-worn configuration, the cold side of each of the TEMs may be positioned adjacent to a skin surface of the wearer, and the hot side of each of the TEMs may be positioned opposite the skin surface of the wearer. When used for heating, the polarity of the opposing surfaces may be reversed such that the first planar surface of the base portion comprises the "hot" side of the TEM and the second planar surface of the flange portion comprises the "cold" side of the TEM. Further, when used for recovery, the polarity of the opposing surfaces may be cycled according to a duty cycle such that, for example, the first planar surface alternates between a "cold" side and a "hot" side. Any and all aspects, and any variation thereof, are contemplated as being within aspects herein. Contact of the first planar surface of the base portion of each of the TEMs with the wearer's skin surface may be facilitated by forming the apparel item with a high degree of elasticity so that the apparel item conforms closely to the wearer's body surfaces (i.e., the apparel item may comprise a compression or base layer).

Once the wearer begins exercising or performing his or her job duties, the wearer's body temperature may rise. Further, the wearer may begin sweating. Due to the apparel item being formed of, for example, a wicking material, the sweat may be transported from a skin-facing side of the apparel item to an outer-facing side of the apparel item. The sweat may then pass through the dimensionally stable frame via the perforations where it is then absorbed by the absorbent material present on the second surface of the frame. A continued rise in the wearer's body temperature may trigger the TEMs to start cycling on and off to help cool the wearer. As described, to improve the efficiency of the TEMs, the heat produced at the hot side of the TEM should be removed. This is accomplished via, for example, evaporative cooling facilitated by the release of the perspiration stored in the absorbent material surrounding the TEMs as well as by the release of perspiration stored in the fabric of the apparel item that covers the hot side of the TEMs after they are releasably mated to the dimensionally stable frame. For instance, because the fabric is a wicking fabric, it may help to transport the perspiration collected in the absorbent material surrounding the TEMs to the hot side of the TEMs. Evaporation of the sweat from the absorbent material surrounding the TEMs and from the fabric positioned adjacent to the hot side of the TEMs helps to transfer heat from the hot side of the TEMs to the ambient environment.

Accordingly, aspects herein disclose an attachment structure for attaching at least one device to an apparel item. The attachment structure comprises a dimensionally stable frame having a first surface and a second surface opposite the first surface, where the dimensionally stable frame having at least one aperture operable to receive the device, and where the first surface of the dimensionally stable frame is affixed to a first surface of the apparel item. The attachment structure further comprises an absorbent material applied to the second surface of the dimensionally stable frame.

In another aspect, an attachment structure for attaching a plurality of devices to an apparel item is provided. The attachment structure comprises a dimensionally stable frame having a first surface and a second surface opposite the first surface, where the dimensionally stable frame comprises a plurality of apertures, each aperture operable to receive a device. The first surface of the dimensionally stable frame is affixed to a first surface of the apparel item.

In yet another aspect, an apparel item having an attachment structure for attaching at least one device to the apparel item is provided. The apparel item comprises a flexible material that forms the apparel item, where the flexible material forms an outer-facing surface and an inner-facing surface of the apparel item. The apparel item further comprises a dimensionally stable frame formed of an absorbent material, where the dimensionally stable frame has a first surface and a second surface opposite the first surface. The first surface of the dimensionally stable frame is affixed to the outer-facing surface of the apparel item at a predetermined location on the apparel item, and the dimensionally stable frame comprises at least one aperture operable to receive the device.

Continuing, another aspect herein provides for an apparel thermo-regulatory system. The apparel thermo-regulatory system comprises 1) an apparel item formed from a flexible material where the apparel item has an outer-facing surface and an inner-facing surface; 2) a dimensionally stable frame having a first surface and a second surface opposite the first surface, where the dimensionally stable frame comprises at least one aperture, and where the first surface of the dimensionally stable frame is affixed to the outer-facing surface of the apparel item at a predetermined location; 3) an absorbent material applied to the second surface of the dimensionally stable frame; and 4) at least one thermoelectric module having a first surface and a second surface opposite the first surface, where the first surface of the thermoelectric module is positioned adjacent to the inner-facing surface of the apparel item and is releasably positioned within the aperture of the dimensionally stable frame.

An additional aspect herein provides for a thermoelectric module array comprising a plurality of thermoelectric modules, each having a first surface and a second surface opposite the first surface. The thermoelectric module array further comprises a flexible substrate having an electronic circuit applied thereto, wherein the flexible substrate is physically and electrically coupled to each of the plurality of thermoelectric modules.

Another aspect described herein provides a thermoelectric module array comprising a plurality of thermoelectric modules, each having a first surface and a second surface opposite the first surface. The thermoelectric module array further comprises a flexible substrate physically and electrically coupled to each of the plurality of thermoelectric modules; the flexible substrate comprising an electrically insulating layer having an electronic circuit applied thereto.

An additional aspect provides for an apparel thermo-regulatory system comprising an apparel item formed from a flexible material and having an outer-facing surface and an inner-facing surface. The apparel thermo-regulatory system further comprises a thermoelectric module array positioned adjacent to the inner-facing surface of the apparel item and releasably coupled thereto, where the thermoelectric module array comprises: 1) a plurality of thermoelectric modules, each having a first surface and a second surface opposite the first surface; 2) a flexible substrate having an electronic circuit applied thereto, wherein the flexible substrate is physically and electrically coupled to each of the plurality of thermoelectric modules; and 3) a power supply unit electrically coupled to the flexible substrate.

As used throughout this disclosure, positional terms used when describing, for instance, an apparel item, such as "anterior," "posterior," "inferior," "superior," "lateral,"

"medial," "inner-facing surface," "outer-facing surface," and the like are to be given their common meaning with respect to the apparel item being worn as intended by a hypothetical wearer standing in anatomical position. Unless indicated otherwise, terms such as "affixed," "coupled," "secured," and the like may mean releasably affixing two or more elements together using for instance, structural differences between the elements, releasable adhesives, snaps, buttons, hook-and-loop fasteners, and the like. These terms may also mean permanently affixing two or more elements together using, for example, stitching, bonding, adhesives, welding, and the like. Unless indicated otherwise, terms such as "proximate" may mean within 0.5 cm to 30 cm of a designated reference point.

Dimensionally Stable Frame

Turning now to FIG. 1, a perspective view of a portion of a textile layer having an exemplary attachment structure is illustrated in accordance with aspects herein and is referenced generally by the numeral 100. In exemplary aspects, the attachment structure may be used to attach one or more rigid-type devices to the textile. As used throughout this disclosure, the term "devices" is meant to encompass devices such as TEMs, radio-frequency identification (RFID) tags, electronic devices such as physiological sensors (heart rate sensors, temperature sensors, respiratory sensors, sweat sensors, and the like), global positioning system (GPS) devices, monitoring devices, power supply units (e.g., batteries) or energy storage devices, lighting devices (e.g., electric light devices having light sources such as LEDs), and the like.

FIG. 1 depicts the textile layer 110 and an attachment structure in the form of a dimensionally stable frame 112. The textile layer 110 may be incorporated into an apparel item and, as such, may generally comprise a flexible material such as a knit or woven material. In an exemplary aspect, the textile layer 110 may comprise a wicking fabric configured to transport moisture from one surface of the textile layer 110 to a second opposite surface of the textile layer 110 using for instance, capillary action, denier differential mechanism, and the like.

The frame 112 is formed of a flexible but dimensionally stable material. In one exemplary aspect, the frame 112 may comprise a thermoplastic polyurethane (TPU) film that may be optionally perforated onto which an optional absorbent material may be applied. In one example, the dimensionally stable frame 112 can be made entirely from TPU. Other materials for the dimensionally stable frame 112 are contemplated herein such as a polyurethane film, a plastic film, a non-woven material, a polystyrene film, a rubber film, a silicone film, a spandex material, and the like. In exemplary aspects, the frame 112 may have a minimum thickness of 100 micrometers. In exemplary aspects, the frame 112 may have a thickness of around 0.5 millimeters although thicknesses greater than this are contemplated herein.

In exemplary aspects, the absorbent material may comprise a hydrogel, a non-woven material such as a spacer mesh or a felt material, a knit pile material, a cellulosic or fiber-based product such as a sponge material, a superabsorbent polymer (SAP), combinations of these materials such as a hydrogel mixed with fibers, and the like. In exemplary aspects, the absorbent material is configured to absorb water and/or sweat equal to at least five times its own volume. Moreover, the absorbent material may be selected such that it releases water (either continuously or intermittently). In some example embodiments, the absorbent material is made entirely of hydrogel. The absorbent material is shown in more detail in FIG. 2. In another exemplary aspect, the frame 112 may be formed from a dimensionally stable absorbent material without a TPU film layer. This is shown in more detail in FIG. 3. Examples of a dimensionally stable absorbent material may comprise, for instance, a non-woven material such as a spacer mesh or a felt material although other dimensionally stable absorbent materials are contemplated herein.

The frame 112 comprises a first surface (not shown) that is integrated into the textile layer 110 by being affixed to a first surface 114 of the textile layer 110. When incorporated into an apparel item, the first surface 114 of the textile layer 110 would form an outer-facing surface of the apparel item. The frame 112 further comprises a second surface 116. A plurality of apertures 118 each defined by an aperture edge 119 extend through the frame 112 but not through the textile layer 110 thus helping to maintain the structural integrity of the textile layer 110. Although the apertures 118 are shown as circular, it is contemplated herein that they may assume different shapes depending on the shape of the device that will be inserted into the apertures 118. For instance, if the device has a triangular profile, then the apertures 118 may have a triangular shape. Any and all aspects, and any variation thereof, are contemplated as being within aspects herein.

Continuing, as shown in FIG. 1, an exemplary pattern of apertures 118 may comprise six apertures 118 radially arranged around a seventh, central aperture 118 in a spoke-and-hub pattern. This is exemplary only, and it is contemplated herein that the apertures 118 may be arranged in a different pattern (e.g., a linear pattern, a staggered pattern, an auxetic pattern, and the like) and/or may comprise fewer or greater than seven apertures. Any and all aspects, and any variation thereof, are contemplated as being within aspects herein. Each aperture 118 may have a diameter 122 between 23.0 mm and 26.0 mm, between 23.3 mm and 25.6 mm, and/or between 23.6 mm and 25.6 mm, although diameters above and below these values are contemplated herein.

Figure 2:
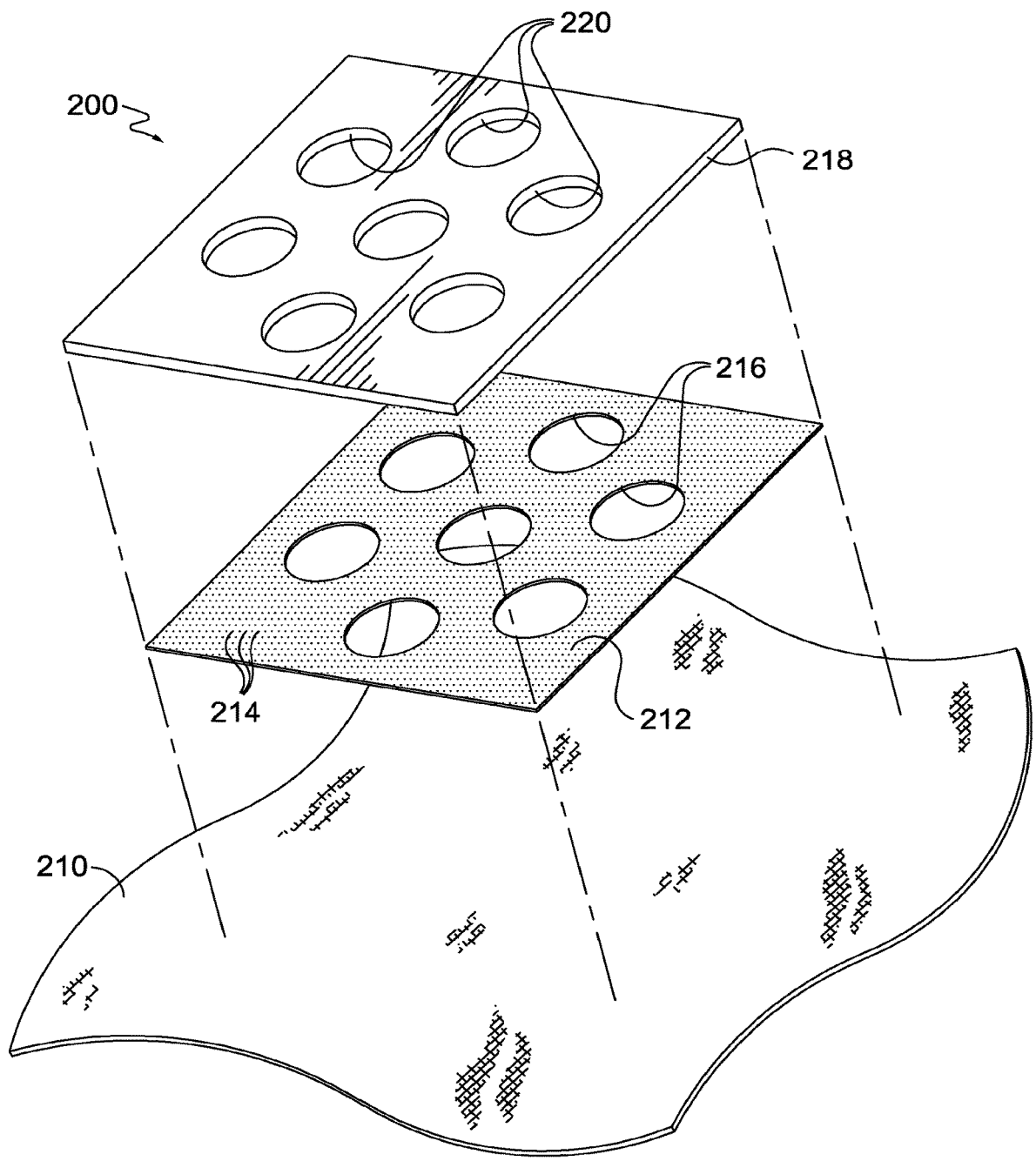
FIG. 2 illustrates an exploded view of the exemplary attachment structure of FIG. 1 in accordance with aspects herein.

FIG. 2 illustrates an exploded view of one exemplary configuration of the attachment structure in accordance with aspects herein and is referenced generally by the numeral 200. FIG. 2 depicts a textile layer 210, a dimensionally stable frame 212, and an absorbent material 218. The textile layer 210 may comprise the textile layer 110 of FIG. 1. The dimensionally stable frame 212 may be formed from, for instance, a flexible TPU or PU film. In exemplary aspects, the frame 212 comprises a plurality of perforations 214 extending therethrough and apertures 216 extending therethrough. The apertures 216 may comprise the apertures 118 of FIG. 1. The perforations 214 are smaller in size than the apertures 216 and may have diameters between, for instance, 1.0 mm and 5.0 mm. The perforations 214, as will be described below, may help perspiration or moisture present on the textile layer 110 to travel through the frame 212 to the absorbent material 218.

With respect to the absorbent material 218, in instances where the absorbent material 218 exhibits some type of dimensional stability such as when the absorbent material comprises a knit pile or a non-woven structure (e.g., spacer mesh, felt), apertures 220 may be formed in the absorbent material 218 or the absorbent material 218 may be formed to comprise the apertures 220. However, in those instances where the absorbent material 218 comprises, for instance, a hydrogel or a SAP that may lack dimensional stability, the absorbent material 218 may not comprise a separate layer having apertures 220, and instead, the absorbent material 218 may be directly applied to the frame 212.

When the attachment structure is assembled, the frame 212 is applied to the surface of the textile layer 210 using for instance, a breathable adhesive, a discontinuous adhesive film (i.e., a film having one or more openings), an adhesive applied in a dot pattern, spot welding, and/or stitching or bonding along the perimeter of each so as not to occlude the perforations 214 and so as not to impede the passage of sweat or moisture from the textile layer 210 to the absorbent material 218. In some instances, the frame 212 may be permanently affixed to the textile layer 210, and in other instances it is contemplated that the frame 212 may be releasably affixed to the textile layer 210.

Continuing, when the absorbent material 218 exhibits dimensional stability, the absorbent material 218 may be permanently or releasably secured to the frame 212 such that the apertures 220 of the absorbent material 218 axially align with the apertures 216 of the frame 212. Securing the absorbent material 218 to the frame 212 may be through a breathable adhesive, a discontinuous adhesive film, an adhesive applied in a dot pattern, spot welding, and/or stitching or bonding along the perimeter of each so as not to occlude the perforations 214 and impede the passage of sweat or moisture from the textile layer 210 to the absorbent material 218. In those instances, where the absorbent material 218 is not dimensionally stable, the absorbent material 218 may be applied to the frame 212 via, for instance, a printing process, a spraying process, a transfer process, a manual application process, and the like.

Figure 3:
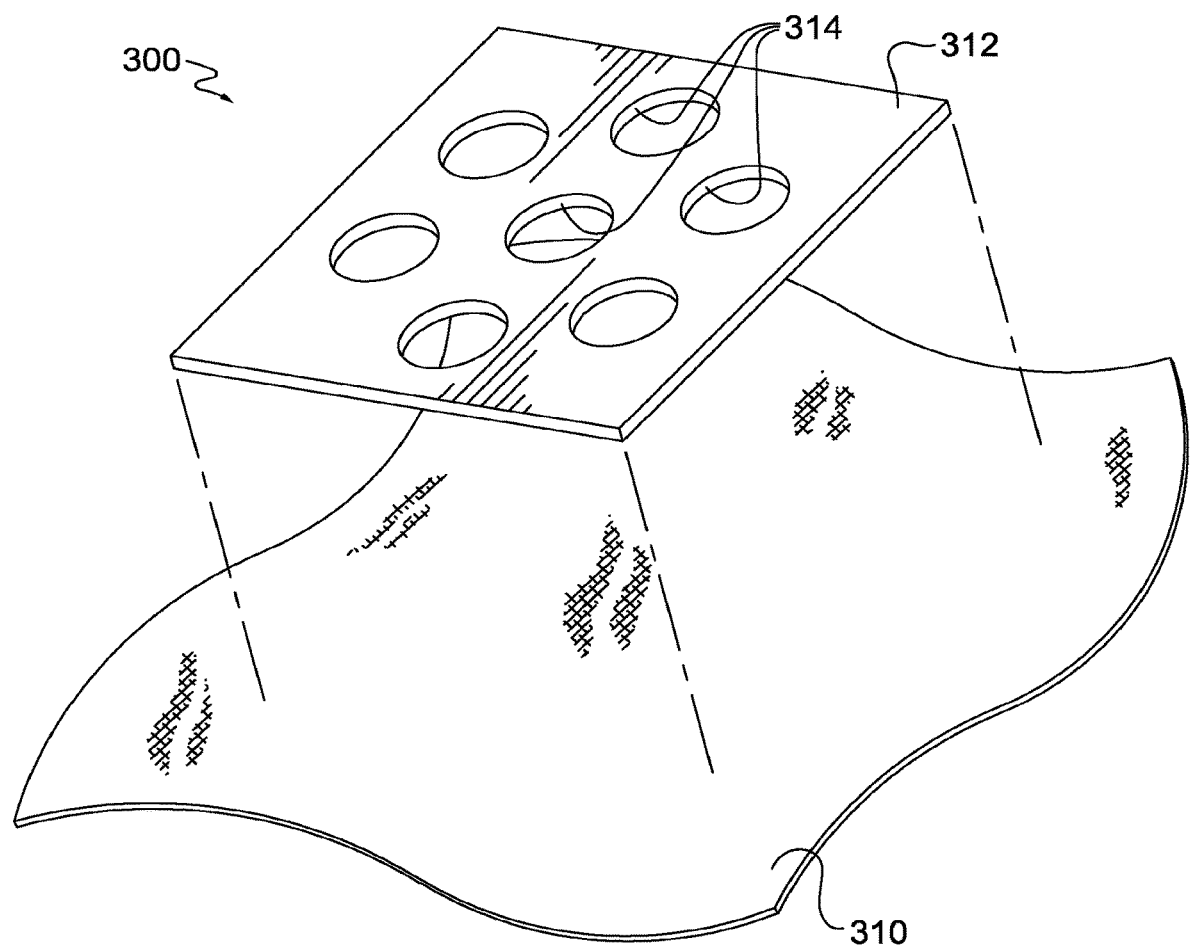
FIG. 3 illustrates an exploded view of an alternative exemplary attachment structure for attaching a device to a flexible material in accordance with aspects herein.

FIG. 3 depicts an exploded view of another exemplary configuration for an attachment structure in accordance with aspects herein and is referenced generally by the numeral 300. The configuration comprises a textile layer 310 which may comprise the textile layer 110 of FIG. 1, and a dimensionally stable frame formed of a dimensionally stable absorbent material 312 such as, for example, a knit pile, a felt, a spacer mesh, other non-woven materials, and the like. Apertures 314, such as the apertures 118, may be formed through the absorbent material 312 or the absorbent material 312 may be pre-formed to comprise apertures 314.

When assembled, the dimensionally stable absorbent material 312 is permanently or releasably applied to the textile layer 310 using, for example, a breathable adhesive, a discontinuous adhesive film, an adhesive applied in a dot pattern, spot welding, and/or stitching or bonding along the perimeter of each so as to permit the free passage of sweat or moisture on the textile layer 310 to the dimensionally stable absorbent material 312.

Figure 4A:
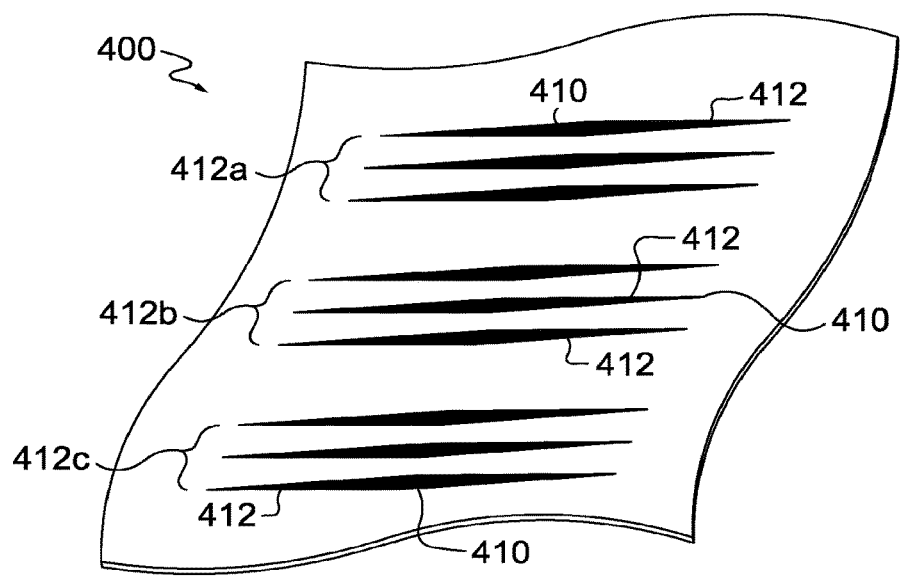
FIGS. 4A and 4B illustrate exemplary patterns of an absorbent material applied to a flexible material in accordance with aspects herein.
Figure 4B:
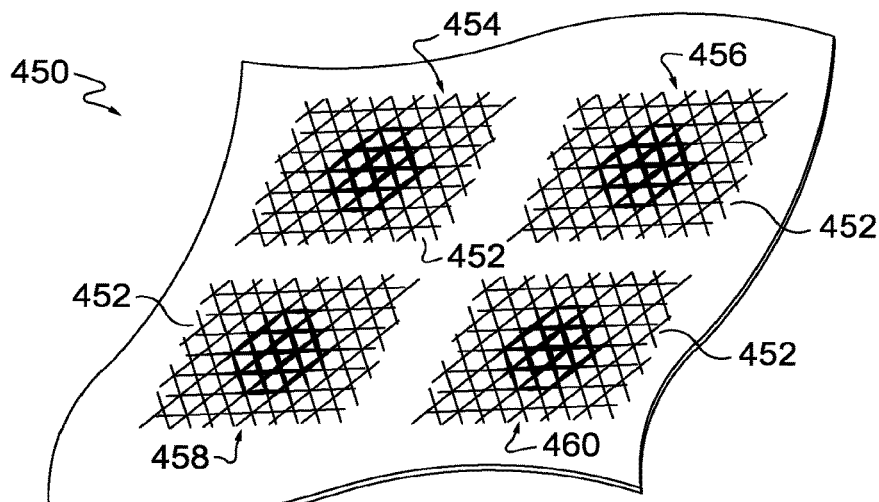
Figure 5:
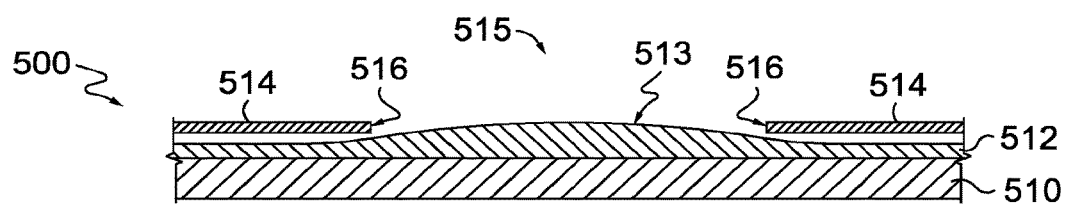
FIG. 5 illustrates a cross-sectional view of a flexible material having an absorbent material applied thereto and an exemplary attachment structure in accordance with aspects herein.

FIGS. 4A, 4B, and 5 depict yet another alternative configuration for the attachment structure in accordance with aspects herein. In some exemplary aspects an absorbent material such as a hydrogel, a hydrogel mixed with fibers, or a SAP may be directly applied to a textile using for instance, a screen printing process, a 3-dimensional printing process, a transfer process, and the like. For instance, FIG. 4A depicts a first surface of a textile 400 to which an absorbent material 410 has been applied in an exemplary pattern. In exemplary aspects, the first surface of the textile 400 may comprise an outer-facing surface of an apparel item when the textile 400 is used to form the apparel item. The pattern shown in FIG. 4A may comprise lines 412 of absorbent material 410 which are thinner at the ends and thicker in the middle. In other words, the volume or quantity of absorbent material 410 may be greater at the middle of the lines 412 as compared to the ends of the lines 412. As shown in FIG. 4A, the lines 412 may be clustered into groups such as line groups 412a, 412b, and 412c. Alternatively, the lines 412 may not be clustered into groups and, instead, may be uniformly distributed on the textile 400. When the textile 400 is incorporated into an apparel thermo-regulatory system, the hot side of a first TEM may be positioned adjacent to the line group 412a, a hot side of a second TEM may be positioned adjacent to the line group 412b, and a hot side of a third TEM may be positioned adjacent to the line group 412c. In each case, the hot side of the TEM may be positioned adjacent to the middle of the lines 412 such that the greatest volume of absorbent material 410 is positioned adjacent to the hot side of the TEM. With respect to the alternative configuration in which the lines 412 are uniformly distributed on the textile 400, one or more TEMs may be positioned such that the greatest volume of absorbent material 410 is positioned adjacent to the hot side of the TEMs.

Another exemplary absorbent material pattern is depicted in FIG. 4B in accordance with aspects herein. FIG. 4B depicts a textile 450 to which an absorbent material 452 has been applied in an exemplary pattern. The pattern in this case comprises a series of intersecting lines clustered into groups such as group 454, group 456, group 458, and group 460. Similar to the pattern shown in FIG. 4A, the lines are generally thinner at each end and thicker in the middle. Because of the intersecting nature of the lines, the greatest volume or quantity of absorbent material 452 may be found at the center of each group 454, 456, 458, and 460. Alternatively, instead of being clustered into groups, the intersecting lines may be distributed across the textile 450 with the greatest volume or quantity of the absorbent material 452 localized generally in the center of the interesting lines. When the textile 450 is incorporated into an apparel thermo-regulatory system, the hot side of a first TEM may be positioned adjacent to the group 454, a hot side of a second TEM may be positioned adjacent to the group 456, a hot side of a third TEM may be positioned adjacent to the group 458, and a hot side of a fourth TEM may be positioned adjacent to the group 460. In each case, the hot side of the TEM may be positioned adjacent to the greatest volume of absorbent material 452 in each group 454, 456, 458, and 460. With respect to the alternative configuration in which the intersecting lines are uniformly distributed on the textile 450, one or more TEMs may be positioned such that the greatest volume of absorbent material 452 is positioned adjacent to the hot side of the TEMs.

The absorbent material patterns shown in FIGS. 4A and 4B are exemplary only and other patterns are contemplated herein. Additionally, the number of absorbent material groupings shown in these figures is exemplary only and a fewer or greater number of groupings is contemplated herein. Each of the absorbent material patterns contemplated herein generally comprise an area with a smaller volume of absorbent material that is contiguous with an area having a greater volume of absorbent material. The areas with a smaller amount of absorbent material may help to channel moisture or sweat to the areas with the greater volume of absorbent material where the moisture or sweat is concentrated and subsequently released.

FIG. 5, referenced generally by the numeral 500, is provided to illustrate how the absorbent material patterns depicted in, for instance, FIGS. 4A and 4B may be utilized in association with an attachment structure for attaching TEMs to a flexible material. More specifically, FIG. 5 depicts a textile layer 510 and an absorbent material 512 applied to a first surface of the textile layer 510. As shown in FIGS. 4A and 4B, the absorbent material 512 may be thinner or have less volume at the periphery of the pattern and be thicker or have more volume at the central portion of the pattern as indicated by the reference numeral 513. A dimensionally stable frame 514 having an aperture 515 defined by aperture edges 516 may be applied to the first surface of the textile layer 510 such that the aperture 515 is positioned over the central portion 513 of the absorbent material pattern (the portion having the greatest volume of absorbent material). When a TEM is positioned adjacent to the second surface of the textile layer 510 and releasably mated to the frame 514, the hot side of the TEM would be positioned adjacent to the central portion 513 of the absorbent material pattern.

Aspects herein further contemplate using hydrophobic treatments applied to a textile to help drive moisture to a desired location. For example, with respect to FIG. 4A, the textile 400 may be formed of a moisture-wicking material and a hydrophobic treatment may be applied to the textile 400. In FIG. 4A, the hydrophobic treatment may be represented by the white areas shown between the black lines 412. In this instance, instead of the lines 412 representing an applied absorbent material 410, they may represent the underlying moisture-wicking textile 400. Or, alternatively, the lines 412 may still represent the applied absorbent material 410. In either instance, the use of the hydrophobic treatment may help to drive or channel moisture to the lines 412 further facilitating the collection of sweat or water at the central portion of the lines 412.

Figure 6:
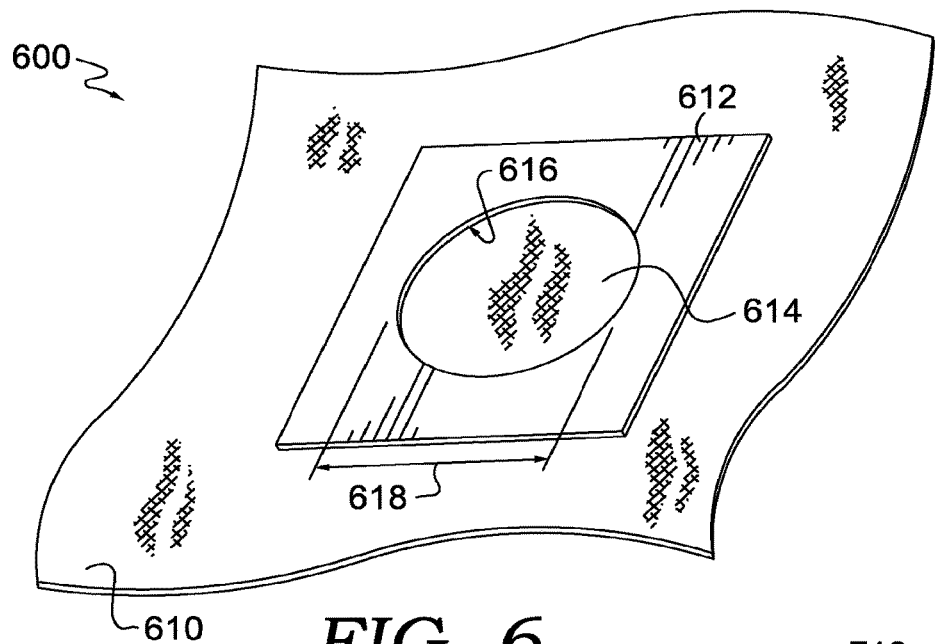
FIG. 6 illustrates a perspective view of an alternative exemplary attachment structure for attaching a single device to a flexible material in accordance with aspects herein.

FIG. 6 depicts an additional exemplary configuration for an attachment structure in accordance with aspects herein and is referenced generally by the numeral 600. FIG. 6 depicts a textile layer 610 to which a flexible, dimensionally stable frame 612 comprising a single aperture 614 defined by apertures edges 616 is applied. The dimensionally stable frame 612 may comprise an absorbent material, or an absorbent material may be applied to the frame 612. The aperture 614 may have diameter 618 sized to receive a larger device such as a larger TEM than those described in relation to, for instance, FIGS. 1-3. In exemplary aspects, the aperture diameter 618 may be between 3.0 to 8.0 cm, 4.0 to 7.0 cm, and/or between 3.0 to 5.0 cm, although diameters above and below these values are contemplated herein. Similar to the configurations described above, the diameter 618 of the aperture 614 may be intermediate between that of the base portion of the larger device and the flange portion of the larger device.

Figure 16A:
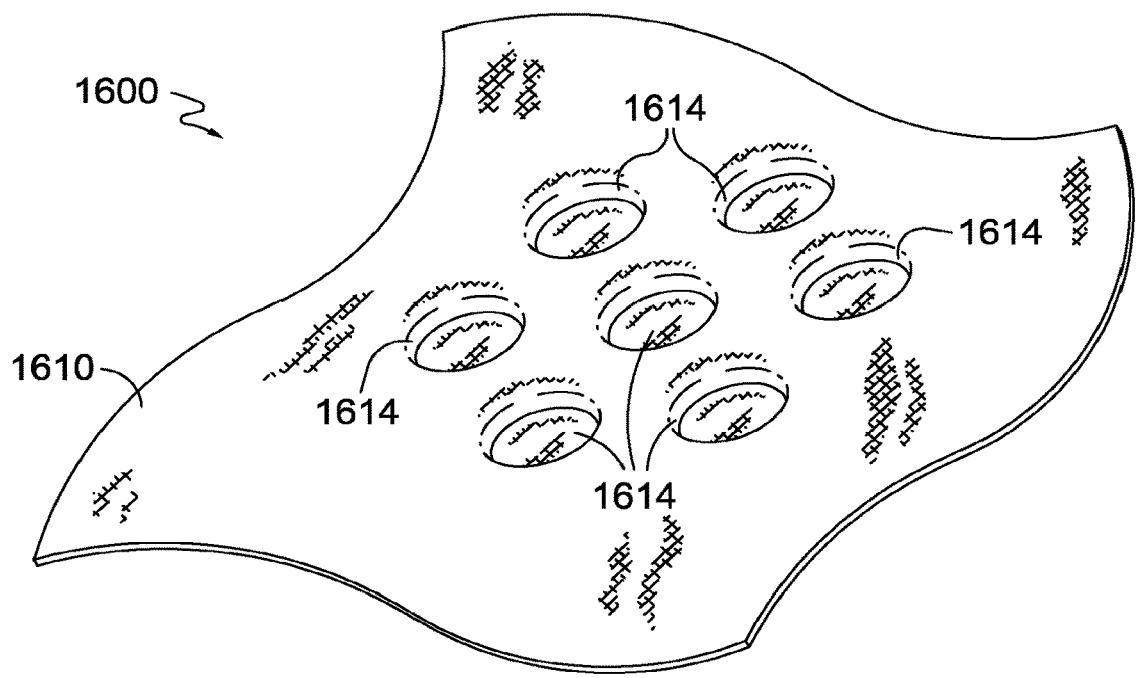
FIGS. 16A-16B illustrate a first and second surface respectively of a flexible textile adapted to receive a device in accordance with aspects herein.
Figure 16B:
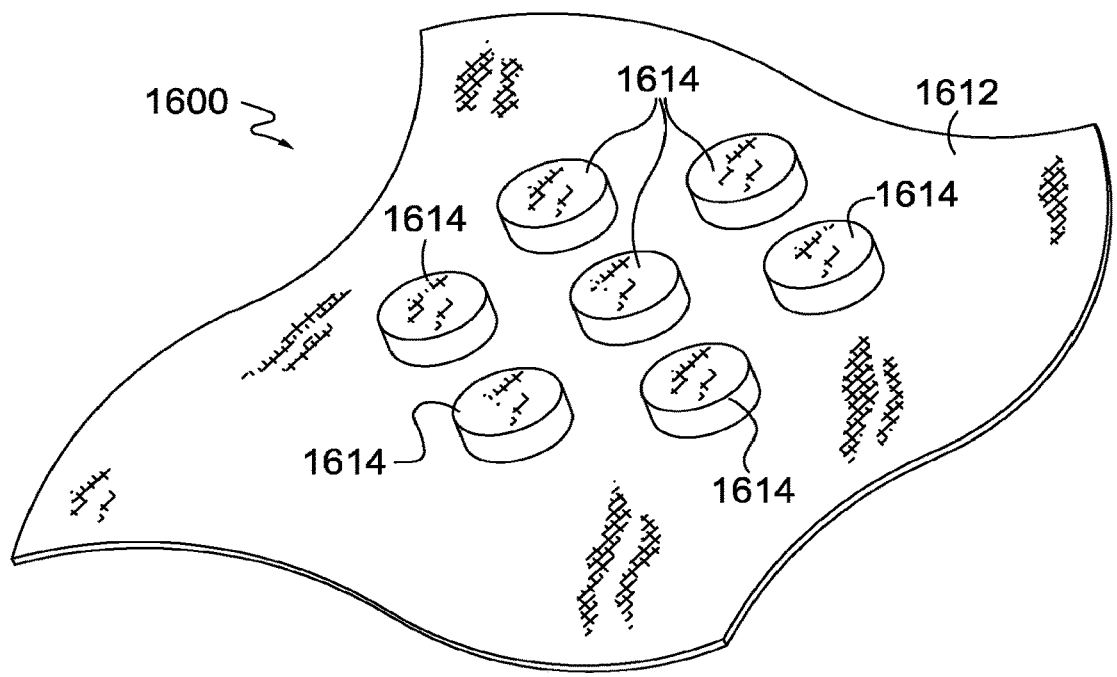

In one exemplary aspect, instead of using a dimensionally stable frame such as those described above, portions of the textile itself may be manipulated to form mating structures designed to receive devices such as TEMs. This aspect is shown in FIGS. 16A and 16B which respectively depict perspective views of a first and second opposing surface of a flexible textile 1600 adapted to receive one or more devices such as TEMs. For instance, FIG. 16A depicts a first surface 1610 of the textile 1600. Mating structures 1614 are shown as depressions or offsets in the negative z-direction from the first surface 1610 of the textile 1600. The mating structures 1614 are arranged in a pattern similar to that shown for the dimensionally stable frame 112 of FIG. 1 although other patterns are contemplated herein. FIG. 16B depicts a second surface 1612 of the textile 1600. In FIG. 16B, the mating structures 1614 are shown as projections or offsets in the positive z-direction from the second surface 1612 of the textile 1600. The projections are complementary to the depressions shown in FIG. 16A. When the textile 1600 is incorporated into an apparel item, the depressions shown in FIG. 16A would be on the inner-facing surface of the apparel item, and the projections shown in FIG. 16B would be on the outer-facing surface of the apparel item. The number and pattern of the mating structures 1614 shown in FIGS. 16A and 16B are exemplary only, and it is contemplated herein that other patterns and numbers of mating structures 1614 may be used.

The mating structures 1614 may be formed by manipulating a knit or weave pattern used to form the textile 1600. The mating structures 1614 may also be created by modifying the type of yarn used to create the textile 1600. For instance a thermosetting yarn may be used such as a thermoplastic polyurethane yarn. A heat molding process may then be used to create the mating structures 1614. In use, the hot side of the TEMs may be positioned within the depressions shown in FIG. 16A. In this instance, the diameter of the TEMs may be slightly greater than the diameter of the mating structures 1614 thus ensuring that the TEMs are retained within the mating structures 1614 once inserted. It is further contemplated herein, that an absorbent material such as a hydrogel or a SAP may be applied to the second surface 1612 of the textile 1600 adjacent to and/or positioned on the projections of the mating structures 1614.

Figure 7:
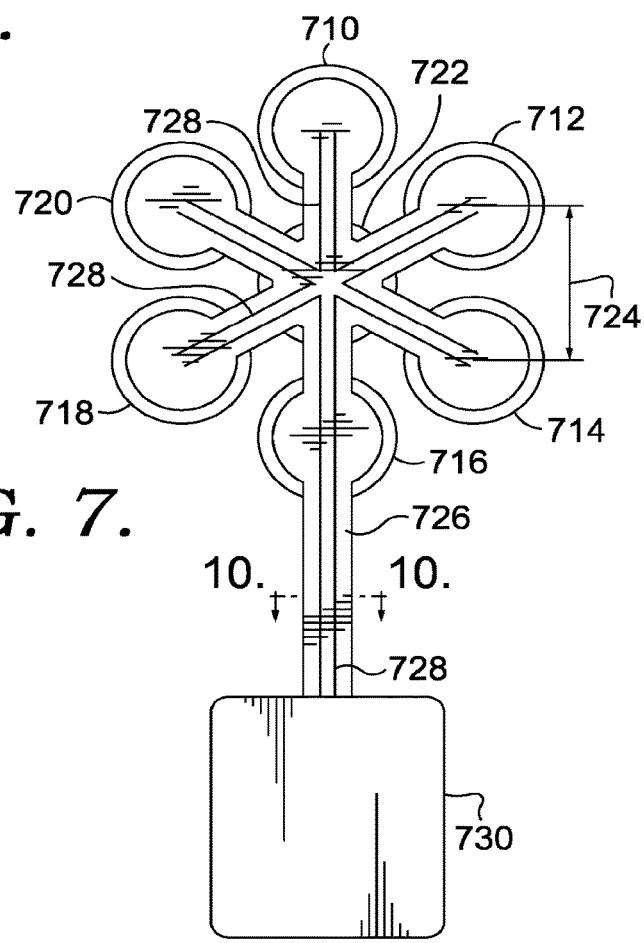
FIG. 7 illustrates a plan view of an exemplary thermoelectric module array in accordance with aspects herein.

The use a flexible, dimensionally stable frame applied to a flexible textile as described herein enables devices, such as TEMs to be easily applied to the textile. Moreover, because of its flexible characteristics as well as its light weight, the dimensionally stable frame may be easily integrated into an apparel item without significantly compromising the weight, pliability, and/or functional characteristics of the apparel item. By applying an absorbent material to the dimensionally stable frame, or by forming the frame from a dimensionally stable absorbent material, such that moisture or sweat is concentrated and released in the areas around the hot side of the TEMs, the frame can play an important role in removing heat from the TEMs thereby improving their efficiency Thermoelectric Module Array Aspects herein further contemplate a thermoelectric module array (TEM array) that can be used as part of an apparel thermo-regulatory system for heating or cooling a wearer. An exemplary TEM array is shown in FIG. 7 and is referenced generally by the numeral 700. In one exemplary configuration, the TEM array 700 comprises device 710, device 712, device 714, device 716, device 718, device 720, and device 722. Each of the devices 712, 714, 716, 718, 720, and 722 may be physically and electrically connected to each other using an electrically insulating film 726 and a flexible electronic circuit 728. Exemplary films may comprise, for example, a polyimide film such as Kapton®, a conductive polyester, a polyether ether ketone (PEEK) and the like. In exemplary aspects, the film 726 may be configured to exhibit stretch characteristics (e.g., two-way stretch and/or four-way stretch). In other words, the film 726, besides being electrically insulating, may be elastomeric. In exemplary aspects, the electronic circuit 728 may be formed on the film 726 using printing and/or photolithographic technology. In another example, the electronic circuit 728 may comprise flexible flat cables (FFCs) that are laminated between layers of the film 726. In one exemplary aspect, the film 726 and the electronic circuit 728 may be physically and electrically coupled to a power supply unit 730 such as a battery unit that is located approximately 4.0 to 8.0 cm from the device 716. The power supply unit 730 may be bi-polar such that it is capable of both heating and cooling.

In exemplary aspects, each of the devices 710, 712, 714, 716, 718, 720, and 722 may comprise a TEM. However, it is also contemplated herein that one or more of the devices 710, 712, 714, 716, 718, 720, or 722 may comprise a power supply unit such as a battery. It is further contemplated herein that one or more of the devices 710, 712, 714, 716, 718, 720, or 722 may comprise a sensor such as a temperature sensor used to detect the temperature of the wearer's skin and/or the temperature of the ambient air. As well, one or more of the devices 710, 712, 714, 716, 718, 720, or 722 may comprise a microprocessor. In some instances, the temperature sensor, microprocessor, and/or power supply unit may be integrated within a TEM.

With respect to the use of microprocessors, the microprocessor may be programmed, for example, to change the polarity of the TEMs such that the cold side of the TEM becomes the hot side and vice versa. The microprocessor may also be programmed to, for instance, cycle the TEM array 700 from an on state to an off state and vice versa based on a duty cycle, based on an input received from a user, and/or based on a temperature detected by the temperature sensor. The microprocessor may additionally be programmed to modulate the amount of current and/or voltage supplied to the TEM array 700 to achieve a pre-defined temperature or temperature range for the hot side or the cold side of the TEM. In one exemplary aspect, the microprocessor may be adapted to communicate with a mobile application via, for instance, Bluetooth®, near-field communication, or other wireless technologies. As such, the microprocessor may be programmed via the mobile application. As well, in an exemplary aspect, the microprocessor may be adapted to communicate with TEMs in the array 700 using Bluetooth®, near-field communication, or other wireless technologies, although wired communication is also contemplated herein.

Continuing, in one example, the microprocessor may be programmed to maintain the cool side of each TEM between 10° C. and 20° C. when the TEMs are used for cooling. When used for heating, the microprocessor may be programmed to maintain the hot side of each TEM between 30° C. and 45° C. in exemplary aspects. Further, the microprocessor may be programmed to alter the polarity of the TEMs in order to cycle one side of the TEM from a cold state to a hot state to promote recovery from, for example, exercise. It is contemplated herein that the microprocessor may be programmed to selectively activate one or more TEMs in the array. For example, a first and second TEM may be activated but not a third and fourth TEM. Other selective activation scenarios are contemplated herein.

An additional programming aspect contemplated herein is the ability to program maximum and/or minimum temperature limits that, when triggered cause the microprocessor to turn off the TEM array 700 entirely or to turn off one or more TEMs in the array 700 to promote wearer safety. For example, a maximum temperature of 50° C. may be set for the hot side of the TEM (i.e., the side exposed to the ambient air) to avoid overheating the TEM. And a maximum temperature of 40° C. may be set for the cold side of the TEM to avoid burning the wearer's skin. A minimum temperature of, for instance, 5° C. may be set for the cold side of the TEM to avoid freezing the wearer's skin. Another safety measure contemplated herein is to limit the maximum voltage of each TEM to less than 12 V to prevent inadvertent electrical shock.

When incorporated as part of an apparel thermo-regulatory system, multiple TEM arrays may be used on an apparel item to provide heating and/or cooling zones to different areas of the apparel item. With respect to this aspect, each TEM array may comprise its own microprocessor and/or sensor. Thus, each array may be independently adjustable to provide customized heating or cooling to different areas of the apparel item.

Figure 9:
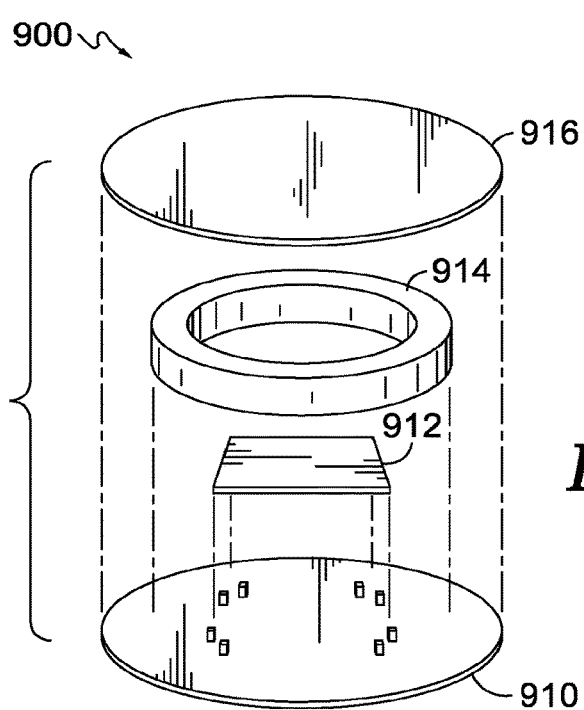
FIG. 9 illustrates an exploded view of an exemplary thermoelectric module in accordance with aspects herein.

When configured as a TEM, each device 710, 712, 714, 716, 718, 720, and 722 may comprise, for instance, a cold side plate, a thermoelectric chip (TEC), an insulating ring, and a hot side plate. This is shown in FIG. 9 which depicts an exploded view of an exemplary TEM 900. As shown in FIG. 9, the TEM 900 may comprise a cold side plate 910 formed from, for instance, anodized aluminum, a sealed TEC 912, an insulating ring 914 formed from, for instance, a closed cell foam material, and a hot side plate 916 formed from, for example, anodized aluminum.

Use of an anodized aluminum on the cold side plate 910 and the hot side plate 916 of the TEM 900 acts as a secondary electrical insulation barrier between the TEC 912 and a wearer's body. The TEC 912 is coated with an electrically insulating material to prevent direct electrical contact with other elements of the TEM 900. The electrically insulating material encasing the TEC 912 also serves as a moisture barrier. The top and bottom plates of the TEC 912 may comprise an electrically insulating alumina ceramic which helps to insulate the top and bottom plates of the TEC 912 from other elements in the TEC 912. Although not shown, any lead wires that connect to the TEM 900 may also be insulated. Additionally, the insulating ring 914 not only provides support from mechanical impact but helps to insulate the hot side plate 916 from the cold side plate 910. It also helps to prevent moisture from entering the TEM 900.

The different components described above may be assembled by seating the TEC 912 on the cold side plate 910 and bonding the hot side plate 916 to the cold side plate 910 via the insulating ring 914 using, for instance, an epoxy. Once assembled, the TEM 900 may be sealed to further reduce the risk of moisture entering the TEM 900.

Figure 8A:
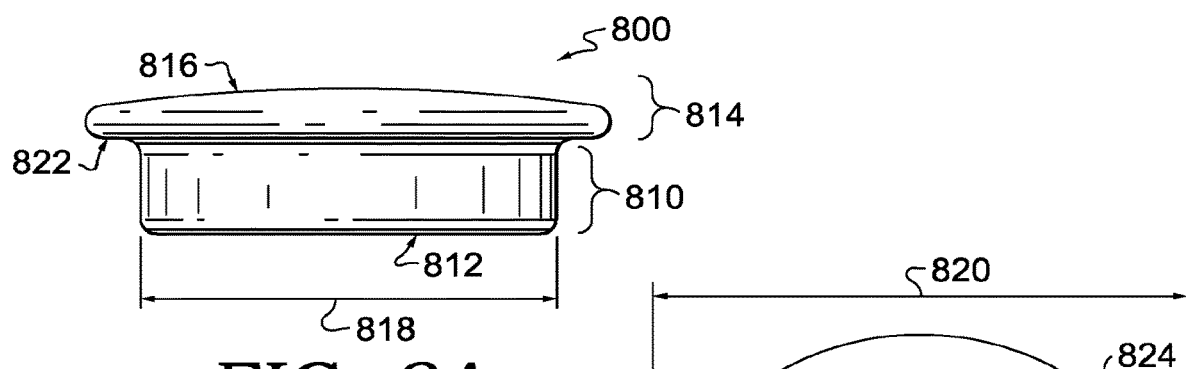
FIG. 8A illustrates a side view of an exemplary thermoelectric module in accordance with aspects herein.
Figure 8B:
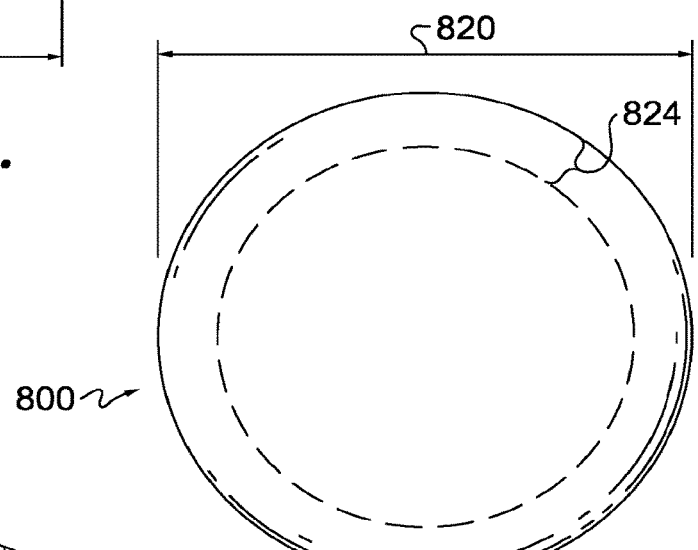
FIG. 8B illustrates a top view of the exemplary thermoelectric module of FIG. 8A in accordance with aspects herein.

A description of the external structure of each of the devices 710, 712, 714, 716, 718, 720, and 722 is provided with reference to FIGS. 8A and 8B. FIG. 8A depicts a side view of an exemplary device 800 such as a TEM, and FIG. 8B depicts a top view of the device 800 in accordance with aspects herein. In exemplary aspects, the device 800 comprises a cylindrical base portion 810 having a first planar surface 812, and a cylindrical flange portion 814 that is contiguous with and radially extends from the cylindrical base portion 810. The flange portion 814 comprises a generally planar second surface 816 opposite the first surface 812. In exemplary aspects, the first surface 812 comprises the cold side of the device 800 when configured as a TEM and the second surface 816 comprises the hot side of the device 800 when configured as a TEM.

In exemplary aspects, the cylindrical base portion 810 may have a diameter 818 between 21.0 mm and 23.0 mm, 22.0 mm and 23.0 mm, 22.4 mm and 22.8 mm, and/or between 22.5 mm and 22.7 mm, although diameters above and below these values are contemplated herein. As seen in FIG. 8B, the flange portion 814 may have a diameter 820 between 27.0 mm and 29.0 mm, 28.0 mm and 29.0 mm, 28.4 mm and 28.8 mm, and/or between 28.5 mm and 28.7 mm, although diameters above and below these values are contemplated herein. In general, the diameter 820 of the flange portion 814 may be approximately 6.0 mm greater than the diameter 818 of the base portion 810. To put it another way, the flange portion 814 may radially extend from the cylindrical base portion 810 by approximately 3.0 mm as indicated by reference numeral 824 in FIG. 8B to form a lip 822 shown in FIG. 8A.

Figure 17A:
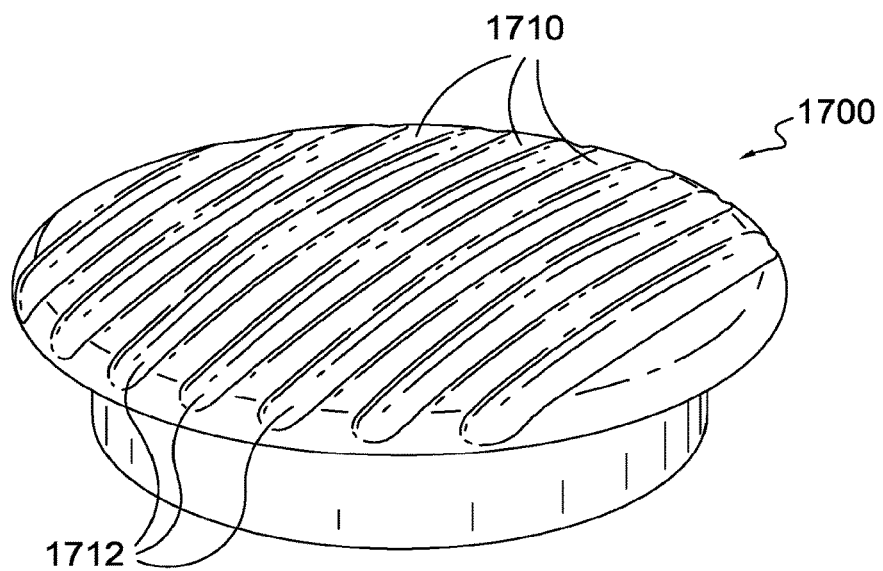
FIG. 17A illustrates a perspective view of an exemplary thermoelectric module having a grooved surface in accordance with aspects herein.

Additional exemplary shape configurations and structures are contemplated for the devices 710, 712, 714, 716, 718, 720, and 722. For example, as shown in FIG. 17A, the second surface 816 of the flange portion 814 may formed to have a series of protuberances 1710 and grooves 1712 to increase its surface area. By increasing the surface area of the second surface 816 (i.e., the hot side of the TEM), the area through which heat may be dissipated from the TEM may be increased further facilitating the efficiency of the TEM.

Figure 17B:
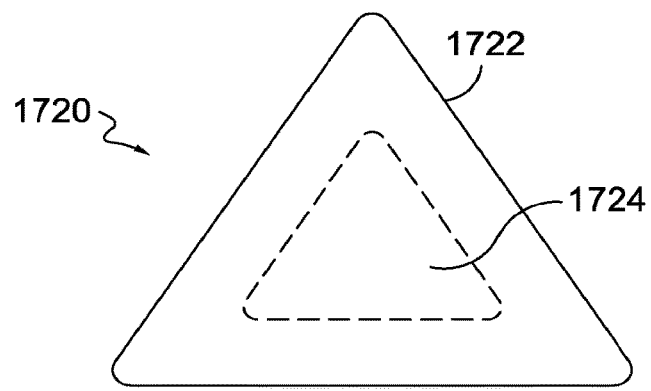
FIGS. 17B-17C illustrate alternative shape configurations for thermoelectric modules in accordance with aspects herein.
Figure 17C:
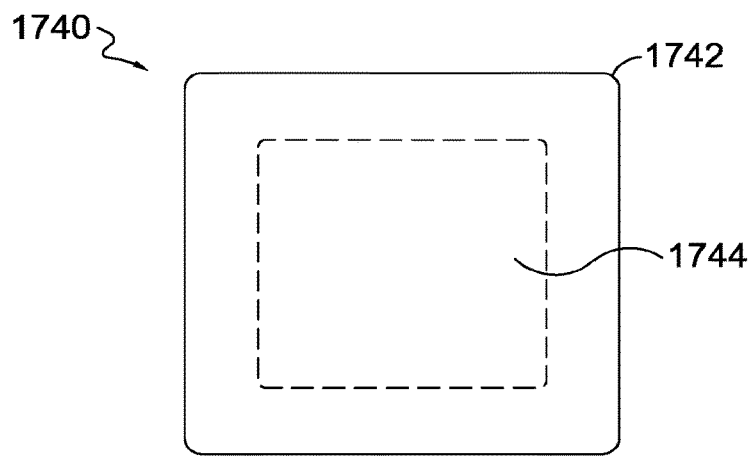

Additional shape configurations for the devices 710, 712, 714, 716, 718, 720, and 722 are shown in FIGS. 17B and 17C in accordance with aspects herein. For instance, FIG. 17B illustrates a top view of a TEM 1720 which illustrates a triangular shape for the TEM 1720. More specifically, the flange portion 1722 of the TEM 1720 has a triangular shape as well as the base portion 1724 of the TEM 1720 (shown by the dashed line). Similar to the device 800 described above, the flange portion 1722 may extend past the base portion 1724 to form a lip useable for securing the TEM 1720 within a similarly shaped aperture of a dimensionally stable frame. FIG. 17C illustrates a top view of a TEM 1740 which illustrates a square shape for the TEM 1740. More specifically, the flange portion 1742 of the TEM 1740 has a square shape as well as the base portion 1744 of the TEM 1740 (shown by the dashed line). Similar to the TEM 1720 described above, the flange portion 1742 may extend past the base portion 1744 to form a lip useable for securing the TEM 1740 within a similarly shaped aperture of a dimensionally stable frame. Other shapes are contemplated herein for the TEMs.

In exemplary aspects, the shape of a TEM may be chosen to preserve the flexibility, drapability, and/or pliability of an apparel item which incorporates the TEM as part of a thermo-regulatory system. For example, by configuring the TEMs to have a triangular shape, a greater number of flexion points between adjacent TEMs may be achieved as compared to, for example, utilizing square-shaped TEMs. This in turn, may help to maintain the pliability of the apparel item.

The device arrays described herein may assume a number of different patterns or configurations. For instance, with respect to FIG. 7, the devices 710, 712, 714, 716, 718, and 720 are radially arranged around the device 722, where the device 722 is located centrally between the other devices 710, 712, 714, 716, 718, and 720 to form a spoke-and-hub pattern. The use of between, for instance, five to seven TEMs arranged in a radial pattern provides for an adequate cooling or heating area when incorporated into an apparel item without significantly compromising the flexibility, drapability, and/or functional characteristics of the apparel item. To provide for an adequate cooling or heating area without having a large footprint, adjacent devices in the array 700 may have a center-to-center offset 724 of between 2.5 cm to 4.0 cm, 3.0 cm to 3.8 cm, and/or between 3.4 cm and 3.6 cm although the center-to-center offset 724 may be greater than or lesser than these values.

Figure 18A:
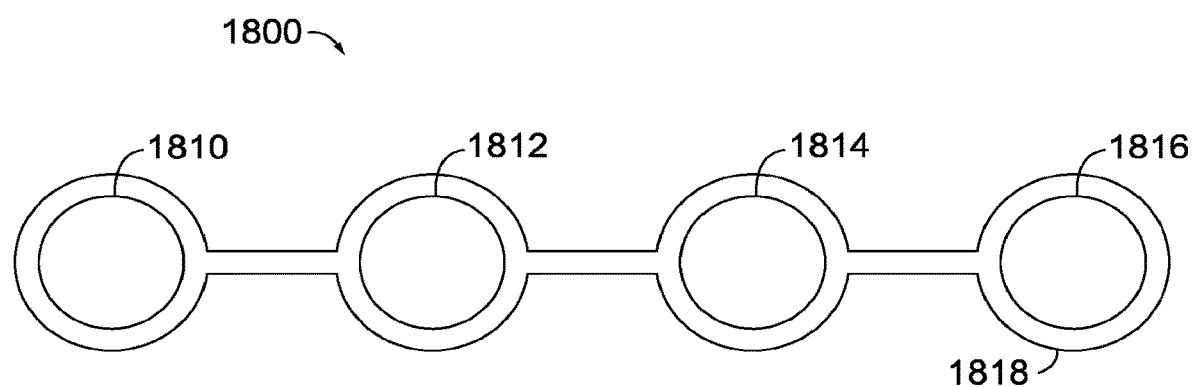
FIG. 18A illustrates an exemplary linear device array in accordance with aspects herein.
Figure 18B:
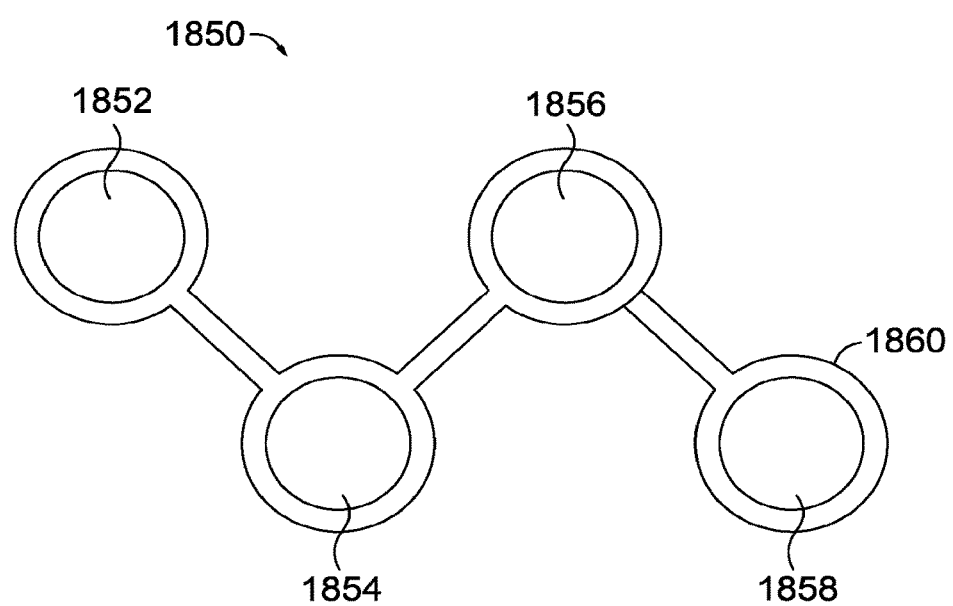
FIG. 18B illustrates an exemplary staggered device array in accordance with aspects herein.

As mentioned, it is contemplated herein that device arrays may assume other patterns such as a linear pattern, a staggered pattern, an auxetic pattern, and the like. For example, FIG. 18A depicts an array 1800 comprising devices 1810, 1812, 1814, and 1816 arranged in a linear pattern in accordance with aspects herein. The devices 1810, 1812, 1814, and 1816 may be physically and electrically coupled using an electrically insulating film 1818. FIG. 18B depicts an array 1850 comprising devices 1852, 1854, 1856, and 1858 arranged in a staggered linear pattern in accordance with aspects herein. The devices 1852, 1854, 1856, and 1858 may be physically and electrically coupled using an electrically insulating film 1860.

Figure 18C:
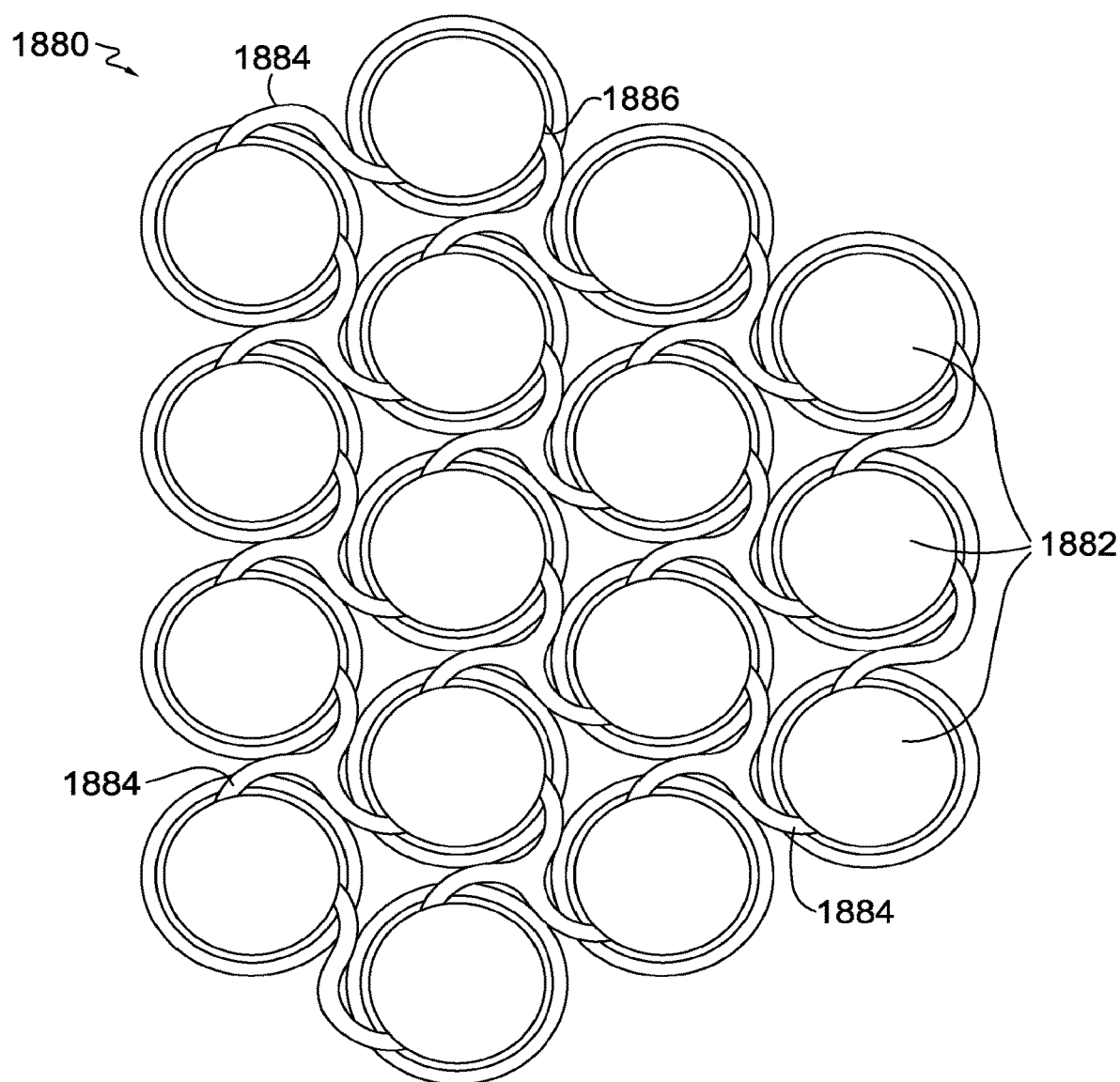
FIGS. 18C-18D illustrate an exemplary auxetic device array in a first state and a second state respectively in accordance with aspects herein.

Continuing, FIG. 18C depicts an array 1880 of devices 1882 configured in an auxetic pattern in accordance with aspects herein. The devices 1882 are located adjacent to each other and are interconnected by a series of spokes 1884. In exemplary aspects, each spoke 1884 may be hingedly attached to a respective device 1882 (as indicated by reference numeral 1886) such that the device 1882 can rotate or pivot in relation to the attachment point of the spoke 1884. In exemplary aspects, the rotation or pivoting of the device 1882 relative to the attachment point of the spoke 1884 occurs in the same plane as the spoke 1884. Depending on the particular spoke configuration, each device 1882 may be connected to up to three to six adjacent devices 1882. In exemplary aspects, the spokes 1884 may comprise an electrically insulating material such as the film 726 of FIG. 7, having or containing a flexible electronic circuit, such as the circuit 728 of FIG. 7. Thus, besides forming a hinged attachment between the devices 1882, the spokes 1884 may also act to electrically interconnect the devices 1882. However, it is also contemplated herein that the devices 1882 may be electrically connected through other means besides the spokes 1884. Any and all aspects, and any variation thereof, are contemplated as being within aspects herein.

Figure 18D:
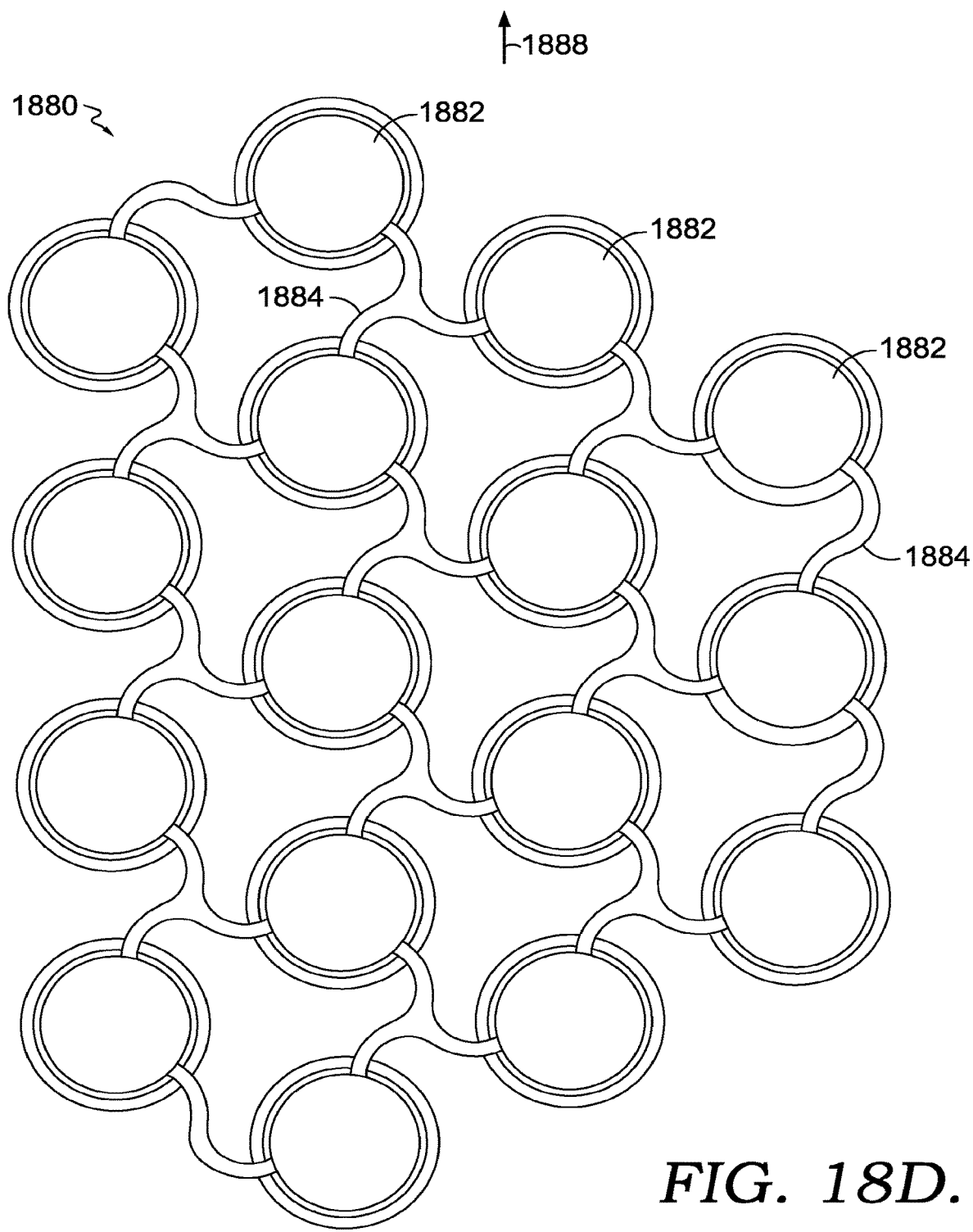

Continuing, the use of the hingedly attached spokes 1884 enables the array 1880 to assume an auxetic pattern (i.e., a pattern or structure that exhibits a negative Possion's ratio that causes the pattern to become thicker in a direction perpendicular to an applied force). For example, as shown in FIG. 18D, a force is applied to the array 1880 as indicated by the arrows 1888. The array 1880 becomes wider in a direction perpendicular to the applied force 1888 due to the devices 1882 pivoting relative to the spokes 1884. The use of an array exhibiting an auxetic pattern, such as the array 1880, may help to increase the flexibility and/or drapability of the array 1880 such that it more easily conforms to a wearer's surface morphology when incorporated into an apparel item.

Selection of a particular device array pattern (e.g., spoke-and-hub, linear, staggered, auxetic, and the like) may be based on the location of the array on an apparel item. For example, and as described in greater detail below, a linear or staggered array of devices may be sufficient for areas of the apparel item that are positioned adjacent to relatively planar body surfaces or areas of the body that do not generate large quantities of heat, or for those areas of the apparel item that undergo little movement such as, for example, the sleeve portions of a shirt. The spoke-and-hub pattern or the auxetic pattern may be used for those areas of the apparel item that are positioned adjacent to more convex or concave body surfaces (shoulders, buttocks, upper chest, and the like) or areas of the body that produce higher quantities of heat, or for those areas of the apparel item that undergo significant flexion/extension during activity. These are just examples, and the positioning of a particular array pattern may differ from those described.

Figure 10:
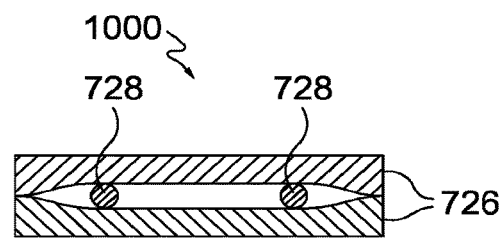
FIG. 10 illustrates a cross-sectional view taken at cut line 10-10 of FIG. 7 in accordance with aspects herein.

Returning generally to FIG. 7, FIG. 10 depicts a cross-sectional view, referenced generally by the numeral 1000, of the film 726 and the electronic circuit 728 taken along cut line 10-10 of FIG. 7 in accordance with aspects herein. As shown, the film 726 encloses and seals the electronic circuit 728 in order to electrically insulate the circuit 728. In exemplary aspects, the film 726 may be optionally positioned between additional film layers. The film layers may comprise, for example, thermoplastic polyurethane, polyurethane, silicone, rubber, plastic, and the like. The additional film layers may be used to as a secondary level of insulation to prevent moisture from contacting the electronic circuit 728. In an exemplary aspect, the film 726 and the additional film layers (if used) may be adhered together through a heat bonding process to seal the resulting structure.

The TEM array described herein provides for a flexible structure that can be incorporated into an apparel item to provide programmable heating, cooling, or recovery features. The array may be sized and configured to enable an adequately sized heating or cooling area while still maintaining the flexibility, drapability, and functional features of the apparel item. Further, the TEM array comprises safety features designed to reduce the risk of electrical shock, burning, and/or freezing.

Apparel Thermo-Regulatory System

Aspects herein contemplate an apparel item having a thermo-regulatory system designed to actively heat or cool a wearer or provide recovery features to the wearer when the apparel item is worn. The thermo-regulatory system may comprise, for instance, an apparel item and one or more TEM arrays positioned on the apparel item at predetermined locations and held in place through use of one or more dimensionally stable frames.

Figure 11:
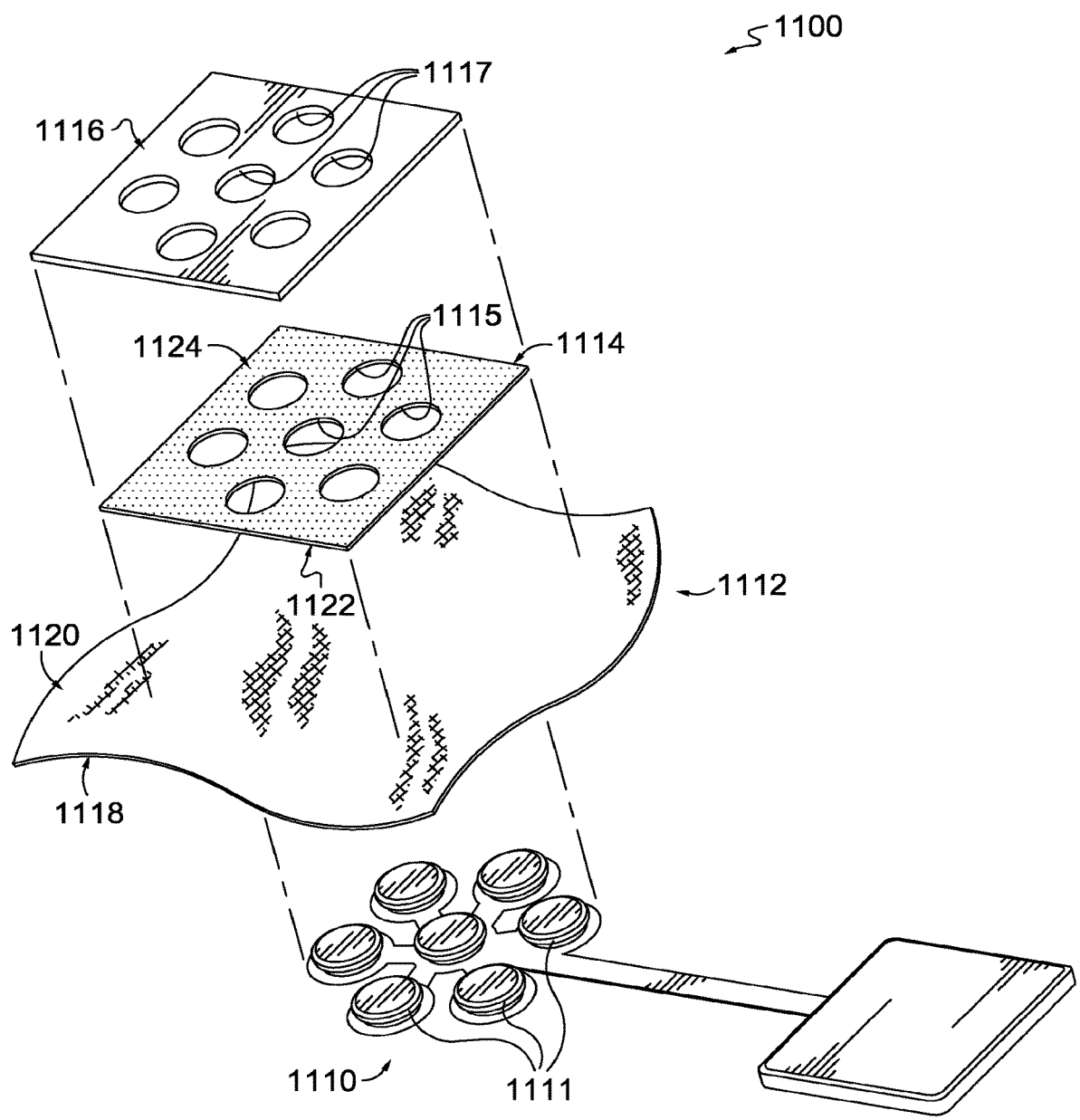
FIG. 11 illustrates an exploded view of an exemplary apparel thermo-regulatory system in accordance with aspects herein.

FIG. 11 illustrates an exploded view of a portion of an apparel thermo-regulatory system 1100 in accordance with aspects herein. In one exemplary aspect, the thermo-regulatory system comprises: 1) a TEM array 1110 having TEMs 1111; 2) a flexible textile 1112; 3) a perforated dimensionally stable frame 1114 having apertures 1115, a first surface 1122, and a second surface 1124; and 4) an absorbent material 1116 having optional apertures 1117. Aspects of the TEM array 1110, the dimensionally stable frame 1114, and the absorbent material 1116 were discussed above. Although the spoke-and-hub pattern is shown with respect to the TEM array 1110, it is contemplated herein that other array patterns may be used as described herein. As well, although the shape of the TEMs 1111 is shown as being circular, it is contemplated herein that other shapes for the TEMs 1111 may be used (e.g., triangular, square, and the like). Any and all aspects, and any variation thereof, are contemplated as being within aspects herein.

As mentioned above, the textile 1112 may comprise a wicking fabric adapted to transport moisture from a first surface 1118 of the textile 1112 to a second surface 1120 of the textile 1112. In use, the second surface 1120 of the textile 1112 would comprise an outer-facing surface of an apparel item and the first surface 1118 of the textile 1112 would comprise an inner-facing surface of the apparel item. As well, the fabric of the textile 1112 may be selected to have a high heat resistance so that it is able to withstand direct contact temperatures of at least 50° C. without deforming and/or without appreciably warming.

In use, the first surface 1122 of the dimensionally stable frame 1114 would be affixed (either releasably or permanently) to the second surface 1120 of the textile 1112, and the absorbent material 1116 would be applied to the second surface 1124 of the dimensionally stable frame 1114. The hot side of the TEMs 1111 in the TEM array 1110 would be positioned adjacent to the first surface 1118 of the textile 1112 such that the TEMs 1111 axially align with the apertures 1115 of the dimensionally stable frame 1114 and/or the apertures 1117 of the absorbent material 1116. Application of an upward pressure to, for instance, the cold side of the TEMs 1111 causes the TEMs 1111 to "snap" into the apertures 1115 of the dimensionally stable frame 1114 and/or the apertures 1117 of the absorbent material 1116 thus releasably securing the TEM array 1110 to the textile 1112 while maintaining the structural integrity of the textile 1112. When no longer needed or before washing the textile 1112, the TEM array 1110 may be removed from the textile 1112 by exerting a downward pressure on the hot side of the TEMs 1111 causing them to disengage from the apertures 1115.

The configuration shown in FIG. 11 is exemplary only and other configurations are contemplated herein. For instance, the configuration shown in FIG. 3 where the dimensionally stable frame is formed of an absorbent material is contemplated herein. Any and all aspects, and any variation thereof, are contemplated as being within aspects herein.

Figure 12:
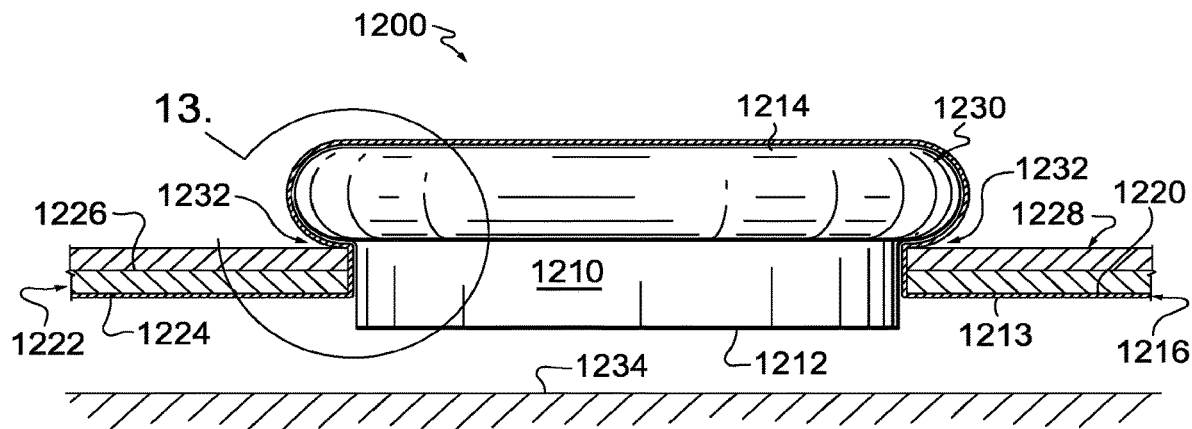
FIG. 12 illustrates a cross-sectional view of a thermoelectric module releasably attached to a flexible material using an attachment structure in accordance with aspects herein.

A view of an isolated TEM after being releasably mated to a dimensionally stable frame is illustrated in FIG. 12 in accordance with aspects herein and is referenced generally by the numeral 1200. FIG. 12 depicts a TEM 1210 having a cold side plate 1212 and a hot side plate 1214 where the cold side plate 1212 is adapted to be positioned adjacent a skin surface 1234 of a wearer. A space is intentionally shown between the cold side plate 1212 and the skin surface 1234 to better illustrate aspects of the configuration. In reality the space between the cold side plate 1212 and the skin surface 1234 would be non-existent or negligible.

FIG. 12 further depicts a flexible textile 1216 having a first surface 1218 and a second opposite surface 1220; a dimensionally stable frame 1222 having a first surface 1224, a second opposite surface 1226, and an aperture defined by aperture edges 1232; and an absorbent material 1228 applied to the second surface 1226 of the dimensionally stable frame 1222. The hot side plate 1214 of the TEM 1210 is positioned adjacent to the first surface 1218 of the textile 1216 (away from the skin surface 1234), and the first surface 1224 of the dimensionally stable frame 1222 is positioned adjacent to the second surface 1220 of the textile 1216. Although the terms "hot side" and "cold side" are used to describe this configuration, it is contemplated herein that the cold side plate 1212 may actually comprise a hot side depending on the polarity of the TEM 1210, and, similarly, the hot side plate 1214 may comprise a cold side. Any and all aspects, and any variation thereof, are contemplated as being within aspects herein.

The TEM 1210 has the structure depicted for the device 800 shown in FIGS. 8A and 8B. For instance, the TEM 1210 has a flange portion comprising the hot side plate 1214, where the flange portion radially extends from a cylindrical base portion comprising the cold side plate 1212 to form a lip 1230 that extends circumferentially around the cylindrical base portion of the TEM 1210. As described with relation to FIGS. 8A and 8B, the diameter of the aperture of the dimensionally stable frame 1222 is intermediate between the diameter of the cylindrical base portion and the diameter of the flange portion of the TEM 1210.

Figure 13:
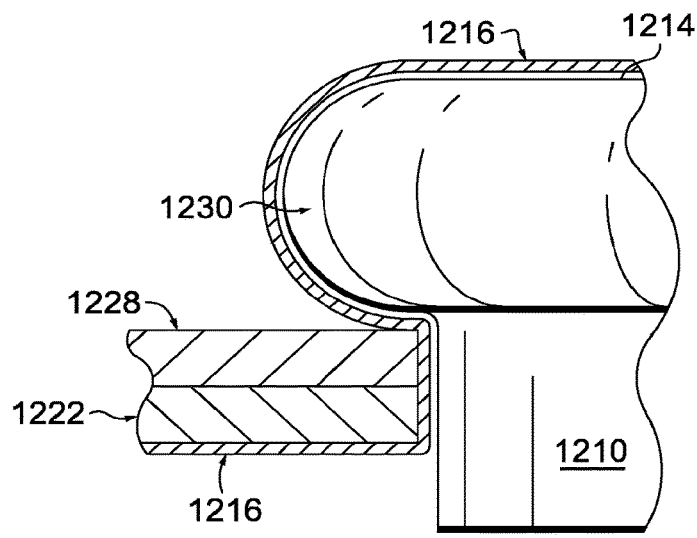
FIG. 13 illustrates a close-up view taken at the area indicated in FIG. 12 in accordance with aspects herein.

FIG. 13 is a magnified view of FIG. 12 taken at the indicated area and illustrating how the lip 1230 of the TEM 1210 helps to secure the TEM 1210 within the dimensionally stable frame 1222. As shown in FIG. 13, once inserted into the aperture of the dimensionally stable frame 1222 via the application of pressure to, for instance, the cold side plate 1212 of the TEM 1210, the lip 1230 rests on the second surface 1226 of the dimensionally stable frame 1222. To remove the TEM 1210 from the dimensionally stable frame 1222, a downward pressure may be applied to the hot side plate 1214 to disengage the TEM 1210. Further, as shown in FIGS. 12 and 13, once mated with the dimensionally stable frame 1222, the textile 1216 covers and/or is positioned adjacent to the hot side plate 1214 of the TEM 1210.

Figure 14:
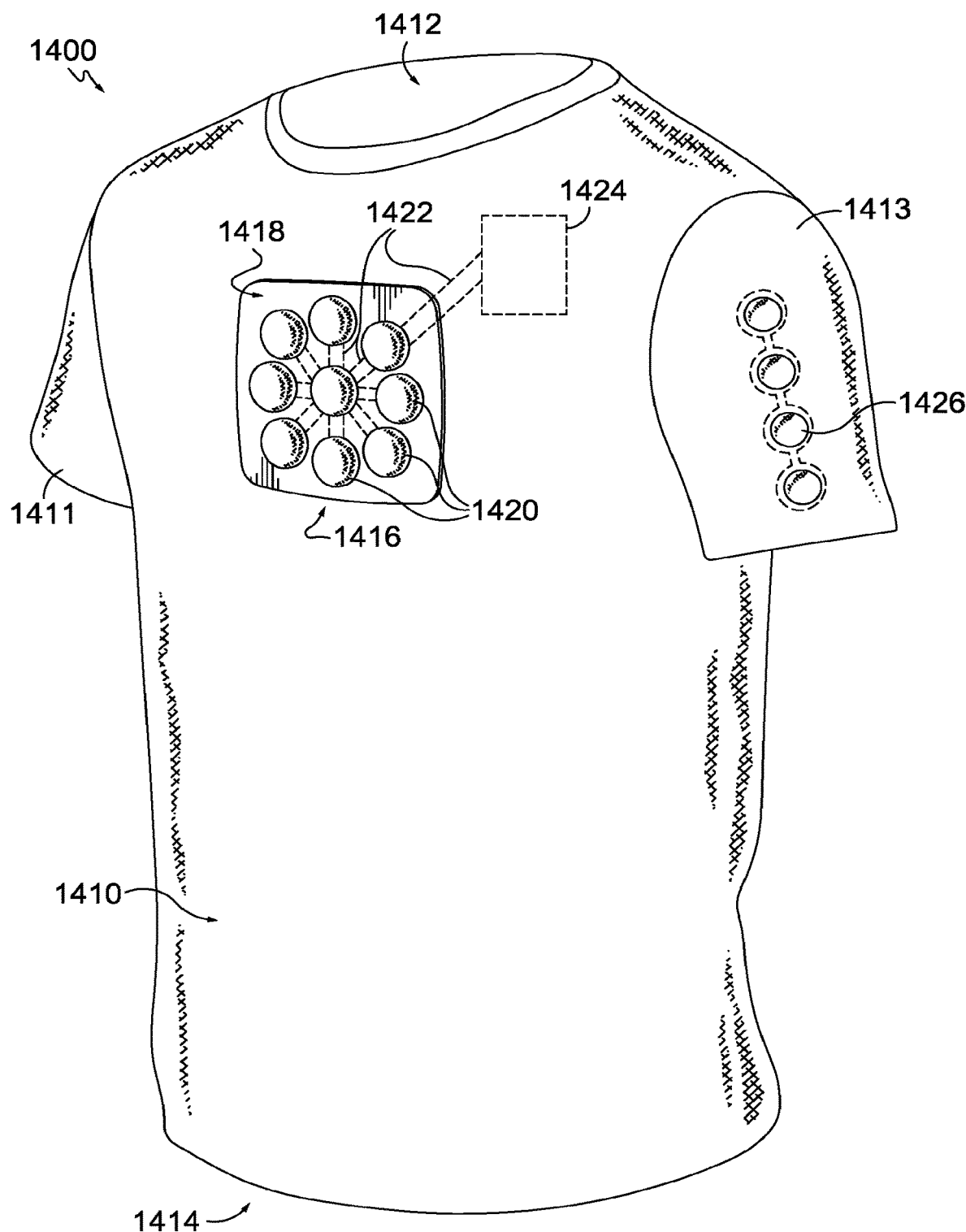
FIG. 14 illustrates a front perspective view of an apparel item having an exemplary apparel thermo-regulatory system in accordance with aspects herein.
Figure 15:
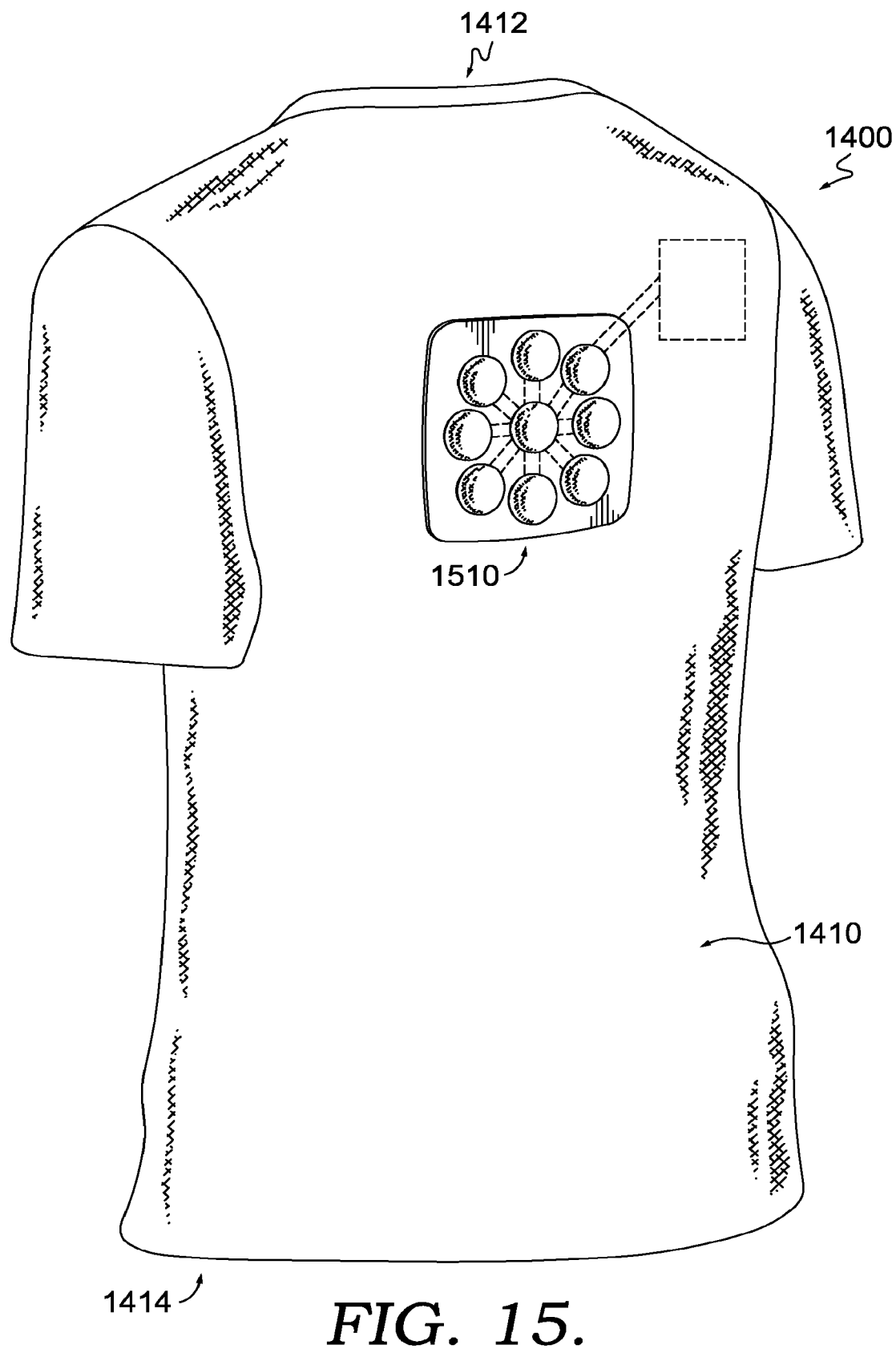
FIG. 15 illustrates a back perspective view of the apparel item of FIG. 14 in accordance with aspects herein.

Turning now to FIGS. 14 and 15, front and back perspective views respectively of an apparel item 1400 having a thermo-regulatory system are depicted in accordance with aspects herein. Although shown in the form of a shirt, it is contemplated herein that the apparel item 1400 may be in the form of a pant, a short, a compression sleeve for an arm or a leg, a headband, a shoe, and the like.

The apparel item 1400 comprises at least a torso portion 1410 (e.g., a front and back portion) adapted to cover a torso area of a wearer when the apparel item 1400 is in an as-worn configuration. The torso portion 1410 defines at least a neck opening 1412 and a waist opening 1414. The apparel item 1400 may also optionally comprise sleeve portions 1411 and 1413 adapted to cover the arms of the wearer when the apparel item 1400 is worn. In exemplary aspects, the apparel item 1400 may comprise a form-fitting apparel item formed of a material exhibiting a moderate to high degree of elasticity such that the apparel item 1400 generally conforms to the body surfaces of the wearer when worn.

A thermo-regulatory system 1416, such as the thermo-regulatory system shown in FIG. 11, is shown positioned on a front aspect of the torso portion 1410 (seen in FIG. 14) proximate to the neck opening 1412, and a thermo-regulatory system 1510 is shown positioned on a back aspect of the torso portion 1410 (seen in FIG. 15) proximate to the neck opening 1412. As used herein, the term "proximate" means within 5 to 25 cm of the neck opening 1412. As well, a thermo-regulatory system 1426 is shown positioned on the sleeve portion 1413 (a similar thermo-regulatory system may also be positioned on the sleeve portion 1411). The thermo-regulatory systems 1416 and 1510 are positioned generally along a vertical midline of the front and back of the apparel item 1400. The areas in which the thermo-regulatory systems 1416 and 1510 are positioned generally correspond to high heat and/or sweat producing areas of a human body as based on, for instance, heat maps and sweat maps. The area in which the thermo-regulatory system 1426 is positioned may generally correspond to a medium to low heat producing area. In exemplary aspects, each thermo-regulatory system 1416, 1510, and 1426 comprises a cooling (or a heating or a recovery) zone on the apparel item 1400.

In exemplary aspects, the thermo-regulatory system 1416 may comprise a dimensionally stable frame 1418 affixed to the apparel item 1400 and into which TEMs 1420 are mated. The film and the electronic circuit 1422 used to physically and electrically couple the TEMs 1420 are shown by dashed lines to indicate they are located on the inner-facing surface of the apparel item 1400. A power supply unit 1424 is also shown as being physically and electrically coupled to the TEMs 1420 via the film and electronic circuit 1422. The power supply unit 1424 is also shown by dashed lines to indicate that it may be located on the inner-facing surface of the apparel item. However, it is contemplated herein that the power supply unit 1424 may be positioned on the outer-facing surface of the apparel item 1400 in some aspects. The power supply unit 1424 may be secured to the apparel item 1400 using, for instance, a pocket, a releasable fastener system such as a loop-and-hook fastener, snaps, buttons, and the like. Further, it is contemplated herein that the power supply unit 1424 may be configured as one of the devices in the TEM array as described above. Thus, the power supply unit 1424 may not comprise a separate unit such as that shown in FIG. 14. Any and all aspects, and any variation thereof, are contemplated as being within aspects herein. The description of the thermo-regulatory system 1416 is equally applicable to the thermo-regulatory system 1510 and the thermo-regulatory system 1426. Additionally, it is contemplated herein that the apparel item 1400 may comprise additional thermo-regulatory systems positioned on the apparel item 1400 in locations corresponding to high to medium heat and/or sweat producing areas. In one example, the apparel item may comprise between 1 and 15 thermo-regulatory systems to provide a corresponding number of heating or cooling zones.

In use, a wearer may independently program the thermo-regulatory system 1416, the thermo-regulatory system 1426, and the thermo-regulatory system 1510 using, for instance, a mobile application. For instance, the wearer may program a temperature set point for the cold side of the TEMs and/or the hot side of the TEMs. The wearer may also program a cycling time for each thermo-regulatory system 1416, 1426, and 1510 (i.e., a time period in which the thermo-regulatory system 1416, 1426, and/or 1516 is in an on state and/or an off state). Cycling the thermo-regulatory systems 1416, 1426, and/or 1510 between an on state and an off state may help to prevent habituation by the wearer. Continuing, the wearer may additionally program a recovery cycle that causes the surface of the TEMs in contact with the wearer's skin surface to alternate between a hot state and a cold state. Any and all aspects, and any variation thereof, are contemplated as being within aspects herein.

Continuing, the wearer would don the apparel item 1400 and begin exercising or begin his or her job duties when used by, for example, firefighters or military personnel. Alternatively, the wearer may don the apparel item 1400 subsequent to exercising in order to cool down and or to promote recovery. As the wearer begins to perspire, the sweat may move from an inner-facing surface of the apparel item 1400 to the outer-facing surface of the apparel item 1400 due to the wicking properties of the textile forming the apparel item 1400. The sweat may then accumulate in the absorbent material deposited on the dimensionally stable frame of the thermo-regulatory systems 1416, 1426, and/or 1510. This process may be helped by perforating the dimensionally stable frame such that the sweat can move from the textile forming the apparel item 1400 to the absorbent material. The accumulation of sweat in the absorbent material is facilitated by positioning the thermo-regulatory systems 1416 and 1510 on the apparel item 1400 in locations positioned adjacent to high sweat-producing areas of the wearer.

Because the absorbent material surrounds and/or is positioned adjacent to the hot side of the TEMs, release of the sweat by the absorbent material and its subsequent evaporation from the hot side of the TEMs helps to remove heat from the TEMs. This, in turn, helps the TEMs to operate more efficiently. For example, by dissipating heat from the hot side of the TEMs, a greater temperature differential can be maintained between the cold side and the hot side of the TEMs. This, in turn, reduces the amount of power needed to run the TEMs.

The use of the wearer's own sweat to dissipate heat from the hot side of the TEMs may be augmented by providing an external liquid source to the hot side of the TEMs. For instance, water may be sprayed or applied to the apparel item 1400 in areas where the thermo-regulatory systems 1416, 1426, and 1510 are located. Evaporation of the water may further help to dissipate heat from the hot side of the TEMs. As well, removal of heat from the hot side of the TEMs via evaporation may be further enhanced by air movement over the thermo-regulatory systems 1416, 1426, and/or 1510 either through intrinsic wearer movement (e.g., running) or by an external wind source such as fans.

It is contemplated herein that additional mechanisms of driving sweat to the thermo-regulatory systems 1416, 1426, and 1510 may be utilized. In one example, wicking threads or yarns may be integrated into the apparel item 1400 such that a first end of the wicking thread is positioned at a location disparate from the thermo-regulatory systems 1416, 1426, and 1510 and a second end of the wicking thread is positioned adjacent the TEMs and/or adjacent to the absorbent material. For instance, a first end of the wicking threads or yarns may be positioned at areas of the apparel item proximate to the waist opening 1414. Thus, sweat generated at a location on the apparel item that is disparate from the thermo-regulatory systems 1416, 1426, and/or 1510 may be transported to the systems 1416, 1426, and/or 1510 using the wicking threads.

Continuing, in another example, some or all of the apparel item 1400 may be formed from a hydrophobic material and hydrophilic channels may be created on the apparel item 1400 via for instance, a process that deposits a hydrophilic material on the apparel item 1400, the use of hydrophilic fabrics, and the like. The channels may be used to transport sweat generated at a location on the apparel item 1400 that is disparate from the thermo-regulatory systems 1416, 1426, and/or 1510 to the systems 1416, 1426, and/or 1510. In an additional example, and as described above with respect to FIG. 4A, a hydrophobic treatment may be applied to the apparel item 1400 in such a way as to force moisture and/or sweat to travel along hydrophilic channels formed by, for instance, a hydrogel or SAP applied to the apparel item 1400 and/or by forming the apparel item 1400 from a moisture wicking fabric. Any and all aspects, and any variation thereof, are contemplated as being within aspects herein.

Besides being used to cool the wearer, the thermo-regulatory systems 1416, 1426, and 1510 may also be used to heat the wearer. For instance, the polarity of the TEMs may be reversed such that the cold side of the TEMs becomes the hot side and the hot side of the TEMs becomes the cold side. As such, the hot side of the TEMs is positioned to be adjacent to a skin surface of a wearer when the apparel item 1400 is worn. Similar to above, the wearer can program the hot side of the TEMs to a desired temperature such as between, for example, 30 to 40° C., set a cycle time, and the like. Instead of heat from the hot side of the TEMs being dissipated to the ambient air, the heat can be dissipated to the wearer's skin surface helping to warm the wearer.

The thermo-regulatory systems 1416, 1426, and 1510 may also be used to help the wearer recover from athletic activities. For instance, the TEMs in the thermo-regulatory systems 1416, 1426, and 1510 may be programmed to cycle from a hot state to a cold state. More particularly, the polarity of the TEMs may be cyclically changed such that the cold side of the TEM becomes the hot side and then cycles back to the cold side according to a programmed schedule.

Figures 19, 20:
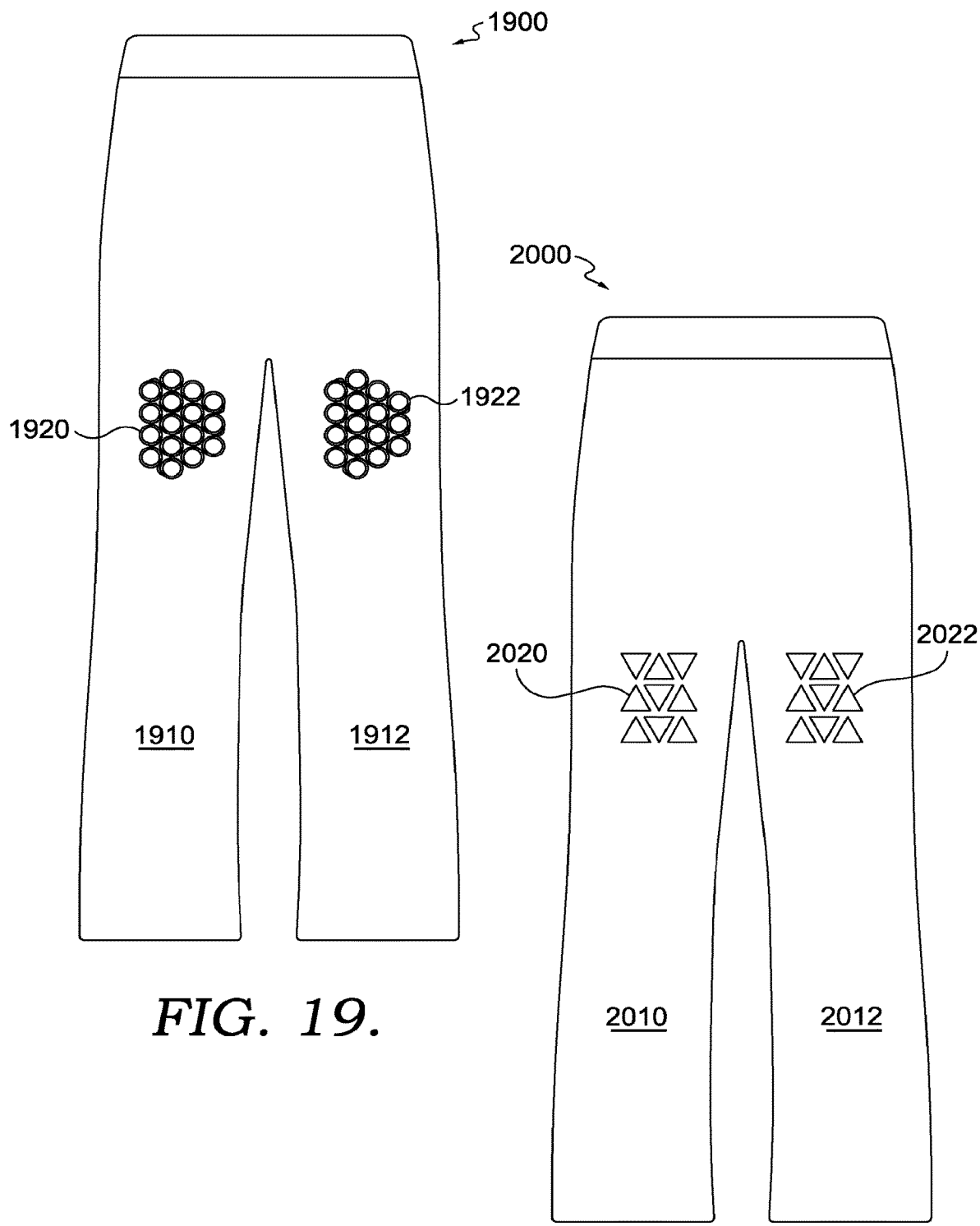
FIG. 19 illustrates a front view of an apparel item having an exemplary apparel thermo-regulatory system in accordance with aspects herein.
FIG. 20 illustrates a front view of an apparel item having an exemplary apparel thermo-regulatory system in accordance with aspects herein.

It is contemplated herein that thermo-regulatory systems may also be incorporated into other apparel items such as pants. An example of this is shown in FIG. 19, which depicts a front view of a pair of pants 1900 having a thermo-regulatory system 1920 positioned at an anterior, upper portion of a first leg portion 1910 of the pant 1900 and a thermo-regulatory system 1922 positioned at an anterior, upper portion of a second leg portion 1912 of the pant 1900. These locations may correspond to the quadriceps muscle groups of a wearer when the apparel item 1900 is worn. In exemplary aspects, these locations may correspond to high heat producing areas of a wearer and, as well, may correspond to muscle groups that may benefit from the recovery features associated with the thermo-regulatory systems described herein (i.e., alternating heating and cooling features).

The thermo-regulatory systems 1920 and 1922 are shown as having an auxetic pattern as described in relation to FIGS. 18C-18D. Although the spokes between adjacent TEMs are shown as being on the outer-facing surface of the apparel item 1900, it is contemplated herein that the TEMs with their associated spokes would be positioned adjacent the inner-facing surface of the apparel item 1900. The depiction shown in FIG. 19 is for illustrative purposes only. Because the thigh area of a wearer is a generally convex, tubular-shaped area, using an auxetic pattern for the thermo-regulatory systems 1920 and 1922 enables the systems 1920 and 1922 to "wrap around" the thigh area of a wearer in order to maintain close contact with the wearer's skin surface and allows the thermo-regulatory systems 1920 and 1922 to flex and extend with wearer movement.

It is contemplated herein that additional thermo-regulatory systems may be used in association with the pants 1900. For example, thermo-regulatory systems may be located on the back of the pant, along the shin/calf areas of the pant, across the buttocks area of the pants, and the like. Moreover, the systems may assume a variety of patterns such as the spoke-and-hub, linear, and staggered patterns described herein. Further, the shape of the TEMs may be different from that shown (e.g., triangular, square, rectangle, and the like). Any and all aspects, and any variation thereof, are contemplated as being within aspects herein.

An example of an apparel thermo-regulatory system that utilizes triangular-shaped TEMs is shown in FIG. 20 in accordance with aspects herein. FIG. 20 illustrates a front view of a pant 2000 having at least a first leg portion 2010 and a second leg portion 2012. A thermo-regulatory system 2020 having triangular-shaped TEMs is located at an upper part of the first leg portion 2010, and a thermo-regulatory system 2022 having triangular-shaped TEMs is located at an upper part of the second leg portion 2012. These locations are exemplary only. As shown, the triangular-shaped TEMs in the thermo-regulatory systems 2020 and 2022 are arranged in a tessellation-type pattern such that there are minimal gaps between adjacent TEMs. Use of such a pattern provides targeted heating or cooling with a minimal footprint (i.e., a higher number of TEMs can be positioned within a small surface area by arranging the triangular-shaped TEMs in a tessellation-type pattern). Moreover, the gaps or spaces between adjacent TEMs in the thermo-regulatory systems 2020 and 2022 may act as flexion/extension areas allowing the systems 2020 and 2022 to conform to a wearer's surface morphology and/or to flex and extend with wearer movement. This both improves wearer comfort and increases the area of contact of the systems 2020 and 2022 with the wearer's skin surface thereby providing more effective heating and cooling. It is contemplated herein that the TEMs may comprise different shapes suitable to form tessellation-type patterns as described herein.

The apparel thermo-regulatory system described herein enables an effective heating/cooling mechanism in the form of TEM arrays to be integrated into an apparel item without significantly comprising the weight and/or integrity of the apparel item as well as the different functional characteristics of the apparel item.

Aspects of the present invention have been described with the intent to be illustrative rather than restrictive. Alternative aspects will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

What is claimed is:

1. An attachment structure for attaching at least one device to an apparel item, the attachment structure comprising:
   a flexible and dimensionally stable frame made entirely of thermoplastic polyurethane and having a first surface and a second surface opposite the first surface, the flexible and dimensionally stable frame having at least one aperture operable to receive the at least one device, the first surface of the dimensionally stable frame adapted to be affixed to a first surface of the apparel item; and
   an absorbent material made entirely of hydrogel and applied to the entire second surface of the dimensionally stable frame.

2. The attachment structure of claim 1, wherein the flexible and dimensionally stable frame has perforations formed therethrough, wherein the perforations are smaller and more numerous than the at least one aperture.

3. The attachment structure of claim 1, wherein the at least one device comprises a thermoelectric module.

4. The attachment structure of claim 1, wherein the first surface of the apparel item comprises an outer-facing surface of the apparel item.

5. An attachment structure for attaching a plurality of devices to an apparel item, the attachment structure comprising:
   a flexible and dimensionally stable frame made entirely of thermoplastic polyurethane and having a first surface and a second surface opposite the first surface, the flexible and dimensionally stable frame comprising a plurality of apertures, each aperture of the plurality of apertures operable to receive a device of the plurality of devices, the first surface of the dimensionally stable frame adapted to be affixed to a first surface of the apparel item, wherein the flexible and dimensionally stable frame has perforations formed therethrough, wherein the perforations are smaller and more numerous than the plurality of apertures; and
   an absorbent material made entirely of hydrogel and applied to the entire second surface of the dimensionally stable frame.

6. The attachment structure of claim 5, wherein each device of the plurality of devices comprises a thermoelectric module.

7. The attachment structure of claim 5, wherein the plurality of apertures comprises at least four apertures.

8. The attachment structure of claim 5, wherein the each aperture of the plurality of apertures has a diameter between 23.6 mm and 26.6 mm.

9. The attachment structure of claim 5, wherein the first surface of the apparel item comprises an outer-facing surface of the apparel item.

* * * * *